US008153599B1

(12) United States Patent
Block

(10) Patent No.: US 8,153,599 B1
(45) Date of Patent: Apr. 10, 2012

(54) COMPOUNDS WITH THE BIOLOGICAL ACTIVITY OF VASOACTIVE INTESTINAL PEPTIDE FOR THE TREATMENT OF PULMONARY AND ARTERIOLAR HYPERTENSION

(75) Inventor: Lutz-Henning Block, Emmendingen (DE)

(73) Assignee: Mondobiotech AG, Stans (CH)

( * ) Notice: Subject to any disclaimer, the term of this patent is extended or adjusted under 35 U.S.C. 154(b) by 1018 days.

(21) Appl. No.: 12/005,516

(22) Filed: Dec. 27, 2007

Related U.S. Application Data

(62) Division of application No. 10/416,822, filed as application No. PCT/EP01/13590 on Nov. 22, 2001, now abandoned.

(30) Foreign Application Priority Data

Nov. 28, 2000 (EP) .................................. 00125935

(51) Int. Cl.
*A61K 38/08* (2006.01)
*A61K 38/16* (2006.01)
*A61P 9/12* (2006.01)
*A61N 1/00* (2006.01)

(52) U.S. Cl. ..................... 514/21.6; 514/21.3; 514/15.7; 530/328; 530/324; 607/44

(58) Field of Classification Search .......................... None
See application file for complete search history.

(56) References Cited

U.S. PATENT DOCUMENTS

| 3,880,826 | A | 4/1975 | Said et al. |
| 3,898,329 | A | 8/1975 | Said et al. |
| 4,179,337 | A | 12/1979 | Davis et al. |
| 4,237,046 | A | 12/1980 | Bodanszky |
| 5,147,855 | A | 9/1992 | Gozes et al. |
| 5,688,499 | A | 11/1997 | Banting et al. |
| 6,031,002 | A | 2/2000 | Wysor et al. |
| 6,630,570 | B1 | 10/2003 | Licha et al. |

FOREIGN PATENT DOCUMENTS

| EP | 0184309 | 6/1986 |
| EP | 0204447 | 12/1986 |
| EP | 0225020 | 6/1987 |
| EP | 0325044 | 7/1989 |
| EP | 0401384 | 12/1990 |
| EP | 0405242 | 1/1991 |
| EP | 0463450 | 1/1992 |
| EP | 0536741 | 4/1993 |
| EP | 0613904 | 9/1994 |
| EP | 0620008 | 10/1994 |
| EP | 0663406 | 7/1995 |
| WO | WO-8905857 | 6/1989 |
| WO | WO-91/06565 | 5/1991 |
| WO | WO 95/27496 | * 10/1995 |
| WO | WO-9527496 | 10/1995 |
| WO | WO-9729126 | 8/1997 |
| WO | WO-9735561 | 10/1997 |
| WO | WO-00/05260 | 2/2000 |
| WO | WO 00/05260 A1 | 2/2000 |
| WO | WO-00/61194 | 10/2000 |
| WO | WO-01/34088 | 5/2001 |

OTHER PUBLICATIONS

Wermuth, Pure and Appl. Chem, 1998, 70, 1129-1143.*
Said, 1991, Annals New York Academy of Sciences, 629, 305-318.*
Rubin, Lewis J., "Primary Pulmonary Hypertension", The New England Journal of Medicine, vol. 336, No. 2, Jan. 9, 1997, pp. 111-117.
Xue, C., "Endothelial Nitric Oxide Synthase in the Lungs of Patients with Pulmonary Hypertension", The New England Journal of Medicine, vol. 333, No. 24, 6 pages.
Hultgardh-Nilsson, A., et al., "Growth-inhibitory properties of vasoactive intestinal polypeptide", Regulatory Peptides, No. 22, 1988, pp. 267-274.
Ishihara, T. et al., "Functional Expression and Tissue Distribution of a Novel Receptor for Vasoactive Intestinal Polypeptide", Neuron, vol. 8, Apr. 1992, pp. 811-819.
Wollman, Y. et al., "Vasoactive intestinal peptide: a growth promotor in neuroblastoma cells", Brain Research, No. 624, 1993, pp. 339-341.
Maruno, K. et al., "VIP inhibits basal and histamine-stimulated proliferation of human airway smooth muscle cells", American J. Physiol, 268, pp. L1047-L1051, 1995.
Dey, R.D., et al., "Localization of VIP-immunoreactive nerves in airways and pulmonary vessels of dogs, cats, and human subjects", Cell and Tissure Research, 220, 1981, pp. 231-238.
Said, S. I., "Vasoactive Intestinal Polypeptide (VIP) in Asthma", Annals New York Academy of Sciences, 629, 1991, pp. 305-318.
Hamasaki, Y. et al., Relaxant action of VIP on cat pulmonary artery: comparison with acetylcholine, isoproterenol, and PGE1, J. Appl. Physiol, 54, 1983, pp. 1607-1611.
Iwabuchi, S. et al., "Vasoactive Intestinal Peptide Causes Nitric Oxide-Dependent Pulmonary Vasodilation in Isolated Rat Lung", Respiration, 64, 1997, pp. 54-58.
Saga, T. et al., "Vasoactive Intestinal Peptide Relaxes Isolated Strips of Human Bronchus, Pulmonary Artery, and Lung Parenchyma", Trans. Assoc. Am. Physicians, 97, 1984, pp. 304-310.

(Continued)

*Primary Examiner* — Cecilia J Tsang
*Assistant Examiner* — Satyanarayana R Gudibande
(74) *Attorney, Agent, or Firm* — Meyertons, Hood, Kivlin, Kowert & Goetzel, P.C.; Eric B. Meyertons

(57) ABSTRACT

The present invention relates to peptides which are highly biologically and pharmacologically active as therapeutic drug for the treatment of diseases related to hypertension, especially in medical interventions involving dilatation and remodeling of arterial blood vessels, either in the pulmonary or in the systemic circulation. The peptides which can be used according to the invention for the treatment of said diseases comprise at least one specific highly conservative amino acid residue sequence which seem to play an important role in connection with pulmonary and arteriolar hypertension events. It could be shown that the known naturally occurring peptides "vasoactive intestinal peptide (VIP)" and "pituitary adenylate cyclase-activating polypeptide (PACAP)", having these specific sequences are potent drugs which can be successfully used for treatment of primary pulmonary hypertension (PPH), secondary pulmonary hypertension (SPH), and hypertension of the systemic circulation. Furthermore, the present invention discloses pharmaceutical compositions useful for treatment of PPH, SPH, and hypertension of the systemic circulation within said methods.

18 Claims, 13 Drawing Sheets

OTHER PUBLICATIONS

Figure 1:
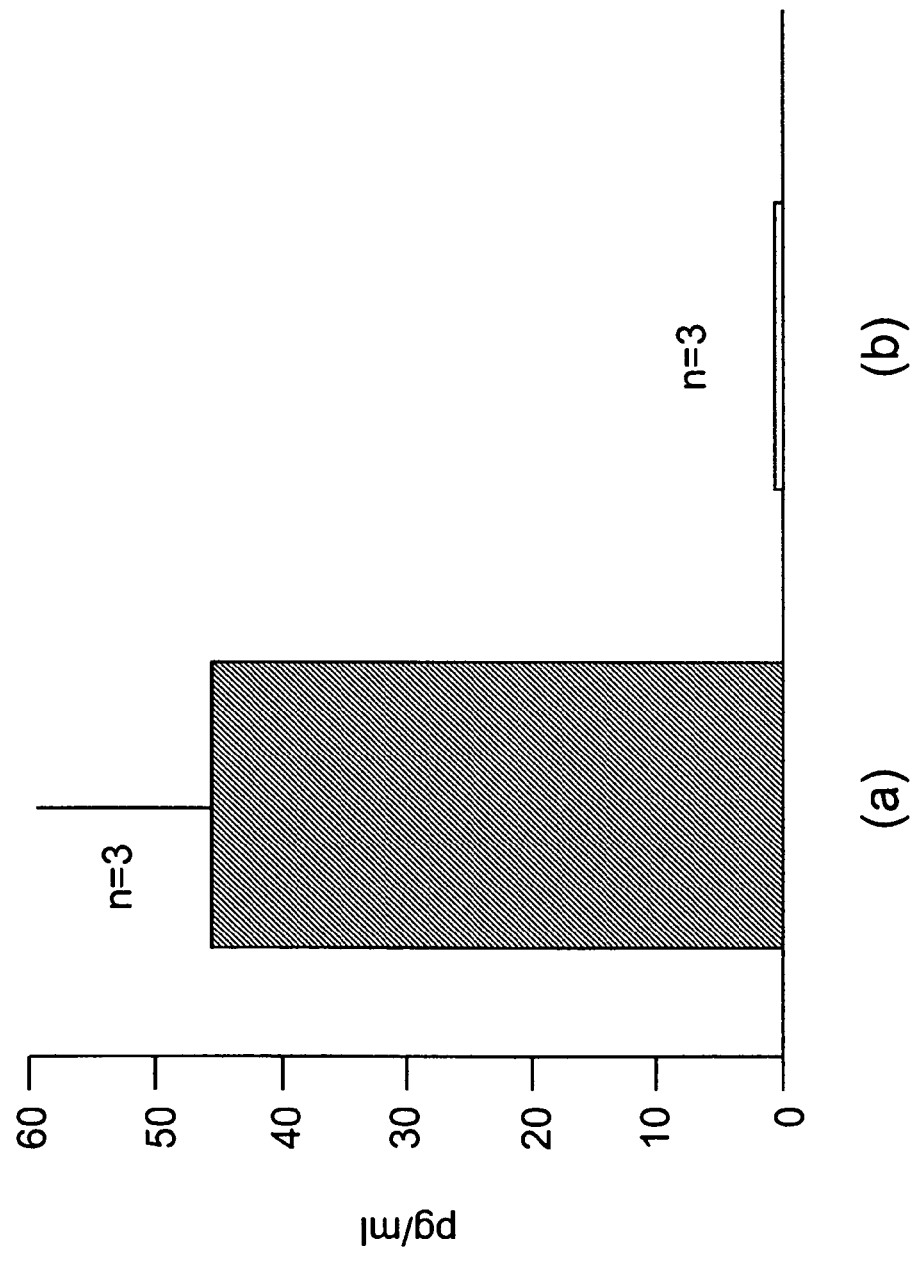

Sada, E. et al., "Resistance to Proteolysis of Antibody Ligands Modified with Polyethylene Glycol", Journal of Fermentation and Bioengineering, vol. 71, No. 2, 1991, pp. 137-139.
Abuchowski, A. et al., "Soluble Polymer-Enzyme Adducts", J.S. Holcerberg and J. Roberts, eds., pp. 367-383, 1981.
Francis, Gillian E., "Protein modification and fusion proteins", Focus on Growth Factors, vol. 3, No. 2, May 1992, (pp. 4-10).
Gennaro, Alfonso R., "Preformulation", Remington's Pharmaceutical Sciences 18th edition, 1990, Mack Publishing Company, Chapter 75, (pp. 1435-1450).
Gennaro, Alfonso R., "Solutions, Emulsions, Suspensions and Extracts", Remington's Pharmaceutical Sciences 18th Edition, 1990, Mack Publishing Company, Chapter 83, (pp. 1519-1544).
Gennaro, Alfonso R., "Powders", Remington's Pharmaceutical Sciences, 18th Edition, 1990, Mack Publishing company, Chapter 88, (pp. 1614-1632).
Gennaro, Alfonso R., "Oral Solid Dosage Forms", Remington's Pharmaceutical Sciences, 18th Edition, 1990, Mack Publishing Company, Chapter 89, (pp. 1633-1665).
Gennaro, Alfonso R., "Aerosols", Remington's Pharmaceutical Sciences, 18th Edition, 1990, Mack Publishing Company, Chapter 92, (pp. 1694-1712).
Keith, I. M., "The Role of Endogenous Lung Neuropeptides in Regulations of the Pulmonary Circulation", Physiological Research, ISSN 0862-8408, 2000, vol. 49, pp. 519-537.
Pavlou, T. A. et al., "Infusion of Vasoactive Intestinal Peptide Improves Hemodynamics in Primary Pulmonary Hypertension", American Review of Respiratory Disease; vol. 14, 1993, pp. A536, suppl. S.
Iwanga, T. et al., "Vasoactive Intestinal Peptide VIP Protects Against Acid-Induced Acute Lung Injury in Isolated Perfused Rat Lungs", Japanese Journal of thoraic Diseases, 1989, XP-002200466 (abstract) (1pg.), Abs in Eng.
Gourlet, Philippe, "C-Terminally shortened pituitary adenylate cyclase-activating peptides (PACAP) discriminate PACAP I, PACAP II-VIP recombinant receptors", Regulatory Peptides, Netherlands, Apr. 23, 1996, XP-002200465 (pp. 125-130).
U.S. Appl. No. 12/005,479, Block.
Gourlet et al., "C-Terminally shortened pituitary adenylate cyclase-activating peptides (PACAP) discriminate (PACAO I, PACAPII-VIP$_1$ and PACAP II-VIP$_2$," Regulatory Peptides, 1996, 62:125-130.
D'Alonzo, G. E. et al. "Survival in Patients with Primary Pulmonary Hypertension". Results from a national prospective registry. Annals of Internal Medicine, vol. 115, No. 5, Sep. 1, 1991 (pp. 343-349).
Palevsky, H. I. et al."Primary Pulmonary Hypertension". Vascular Structure, Morphometry, and Responsiveness to Vasodilator Agents. circ.ahajournals.org., Sep. 10, 2008 (pp. 1207-1221).
Wagenvoort, C. A. et al., "Primary Pulmonary Hypertension". A Pathologic Study of the Lung Vessels in 156 Clinically Diagnosed Cases. Circulation, vol. XLII, Dec. 1970 (pp. 1163-1184).
Wood, P. "Pulmonary Hypertension with Special Reference to the Vasoconstrictive Factor". Jul. 2, 1958 (pp. 557-570).
Giaid, A. et al. "Reduced Expression of Endothelial Nitric Oxide Synthase in the Lungs of Patients With Pulmonary Hypertension". The New England Journal of Medicine Jul. 27, 1995 (pp. 214-221).
Moody, Terry W. et al., "A vasoactive intestinal peptide antagonist inhibits non-small cell lung cancer growth". vol. 90, May 1993 (pp. 4345-4349).
Raderer, M. et al., "Iodine-123—Vasoactive Intestinal Peptide Receptor Scanning in Patients with Pancreatic Cancer". The Journal of Nuclear Medicine vol. 39, No. 9, Sep. 1998 (pp. 1570-1575).
Raderer, M. et al., "Value of Peptide Receptor Scintigraphy Using (123) I-Vasoactive Intestinal Peptide and (111) In—DTPA—D Phe 1—Octreotide in 194 Carcinoid Patients: Vienna University Experience, 1993 to 1998". Journal of Clinical Oncology, vol. 18, No. 6, Mar. 2000, (pp. 1331-1336).
Virgolini, I. et al., "Vasoactive Intestinal Peptide Receptor Scintigraphy". The Journal of Nuclear Medicine vol. 36, No. 10, Oct. 1995 (pp. 1732-1739).
Williamson et al. "Hemodynamic Effects of Bosentan, an Endothelin Receptor Antagonist, in Patients With Pulmonary Hypertension" 2000, Circulation, 102:411-418.
Van Dongen et al. "Calcium Dependence of the Inhibitory Effect of Angiotensin on Renin Secretion in the Isolated Perfused Kidney of the Rat" Br. J. Pharmac. (1974), 50, 125-129.
Northover "Effect of anti-inflammatory drugs on the binding of calcium to cellular membranes in various human and guinea-pig tissues" Br. J. Pharmac. (1973), 48, 496-504.
Cardell et al., "The induction of nitric oxide-mediated relaxation of human isolated pulmonary arteries by PACAP," British Journal of Pharmacology, 1997, 120:1096-1100.
Cheng et al., "Comparison of responses to pituitary adenylate cyclase activating peptides 38 and 27 in the pulmonary vascular bed of the cat," European Journal of Pharmacology, 1993, 243:79-82.
Iwabuchi et al., "Effects of vasoactive intestinal peptide on pulmonary vasoreactivity in isolated perfused rat lungs," Respiration, 1995, 14(5):553-557 (English abstract on last page).
Iwanaga et al., "Vasoactive Intestinal Peptide (VIP) Protects Against Acid-Induced Acute Lung Injury in Isolated Perfused Rat Lungs," Journal of Japan Breast Disease Society, 1989, 27(7):789-795 (English abstract on last page).
Kawasaki et al., "The mechanisms of the relaxation induced by vasoactive intestinal peptide in the porcine coronary artery," British Journal of Pharmacology, 1997, 121:977-985.
Sata et al., "Vasoactive Intestinal Polypeptide Relaxes Pulmonary Artery by an Endothelium-Independent Mechanism," Peptides, 1986, 7(Suppl):225-227.
Warren et al., "Pituitary adenylate cyclase-activating polypeptide: a novel, long-lasting endothelium-independent vasorelaxant," European Journal of Pharmacology, 1991, 197:131-134.

* cited by examiner

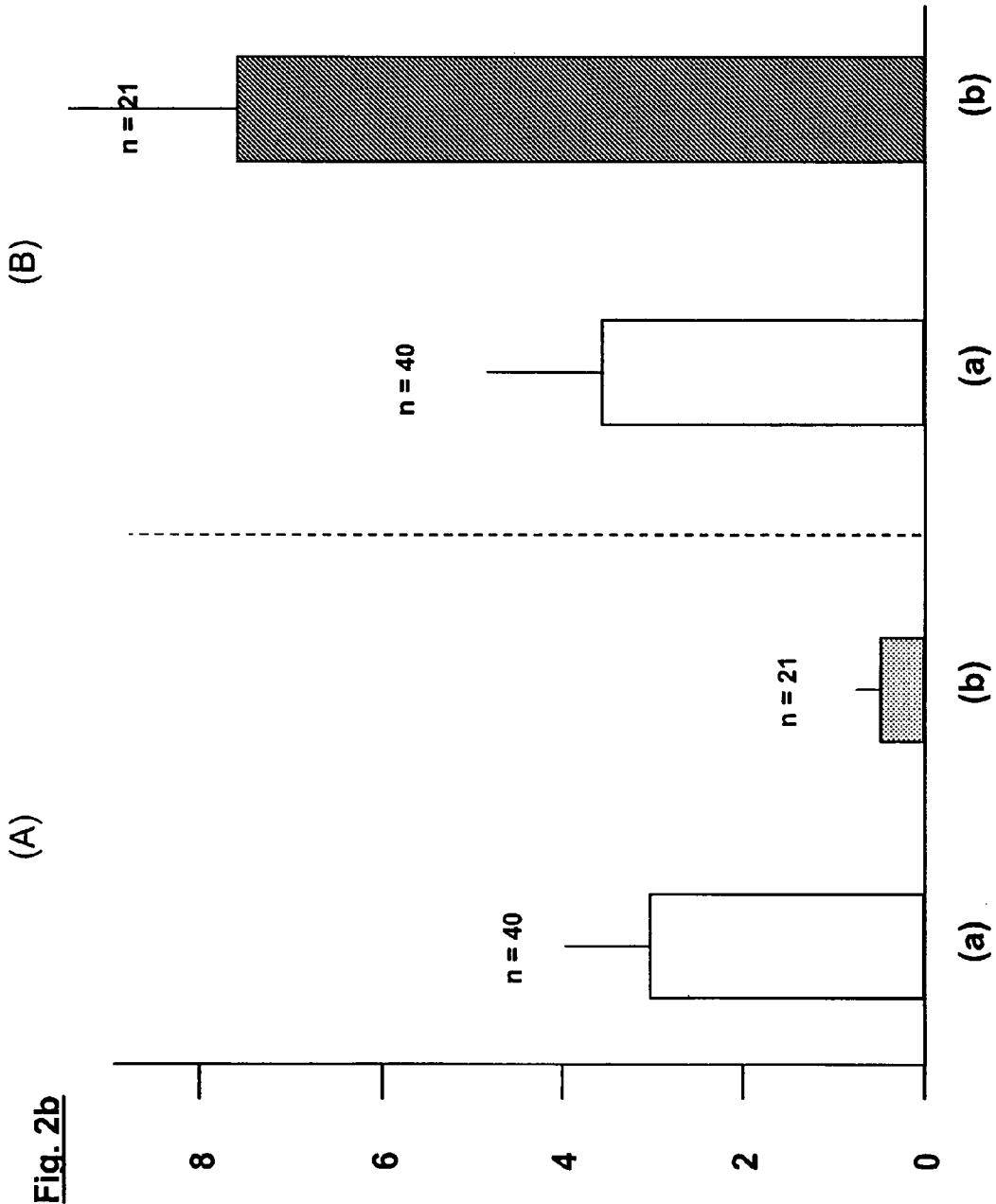

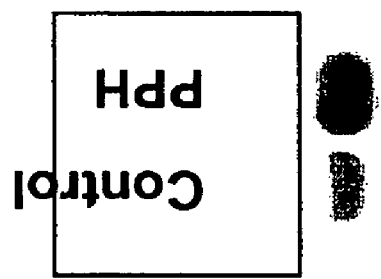
Fig. 3 Transcription of VIP-R1 in lung tissue from normals and PPH patients

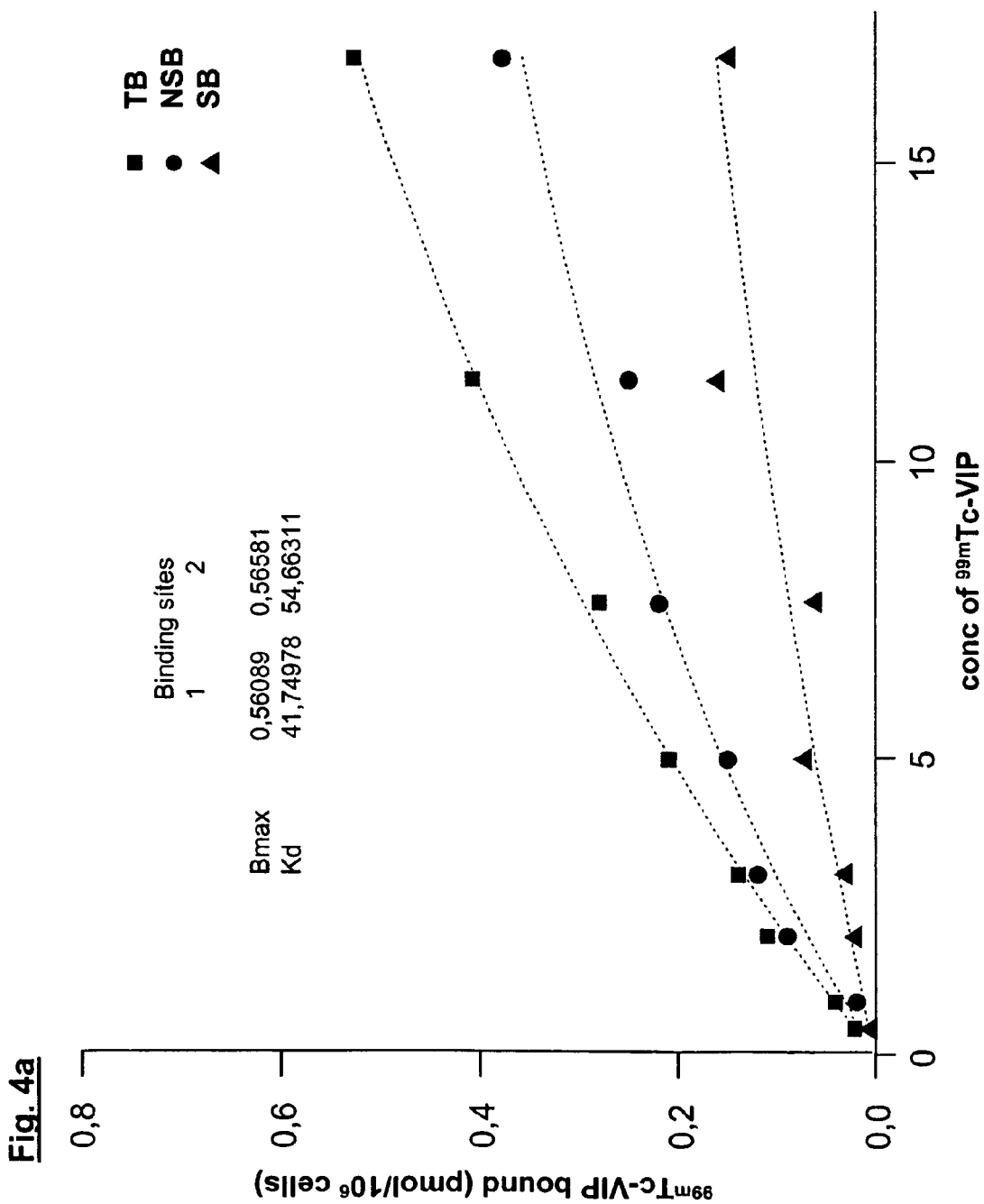

SEQUENCE LISTING

<160> NUMBER OF SEQ ID NOS: 14

<210> SEQ ID NO 1
<211> LENGTH: 28
<212> TYPE: PRT
<213> ORGANISM: Homo sapiens

<400> SEQUENCE: 1

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 2
<211> LENGTH: 38
<212> TYPE: PRT
<213> ORGANISM: Homo sapiens

<400> SEQUENCE: 2

His Ser Asp Gly Ile Phe Thr Asp Ser Arg Tyr Ser Arg Tyr Arg Lys
1               5                   10                  15

Gln Met Ala Val Lys Lys Tyr Leu Ala Ala Val Leu Gly Lys Arg Tyr
            20                  25                  30

Lys Gln Arg Val Asn Lys
        35

<210> SEQ ID NO 3
<211> LENGTH: 27
<212> TYPE: PRT
<213> ORGANISM: Homo sapiens

<400> SEQUENCE: 3

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu
            20                  25

<210> SEQ ID NO 4
<211> LENGTH: 10
<212> TYPE: PRT
<213> ORGANISM: Homo sapiens

<400> SEQUENCE: 4

Arg Lys Gln Met Ala Val Lys Lys Tyr Leu
1               5                   10

<210> SEQ ID NO 5
<211> LENGTH: 23
<212> TYPE: PRT
<213> ORGANISM: Homo sapiens
<220> FEATURE:
<221> NAME/KEY: MISC_FEATURE
<222> LOCATION: (4)..(8)
<223> OTHER INFORMATION: X is any naturally occurring amino acid residue

<400> SEQUENCE: 5

Phe Thr Asp Xaa Xaa Xaa Xaa Xaa Arg Lys Gln Met Ala Val Lys Lys
1               5                   10                  15

Tyr Leu Asn Ser Ile Leu Asn
            20

<210> SEQ ID NO 6

```
<211> LENGTH: 23
<212> TYPE: PRT
<213> ORGANISM: Homo sapiens

<400> SEQUENCE: 6

Phe Thr Asp Asn Tyr Thr Arg Leu Arg Lys Gln Met Ala Val Lys Lys
1               5                   10                  15

Tyr Leu Asn Ser Ile Leu Asn
            20

<210> SEQ ID NO 7
<211> LENGTH: 18
<212> TYPE: PRT
<213> ORGANISM: Homo sapiens

<400> SEQUENCE: 7

Phe Thr Asp Ser Tyr Ser Arg Tyr Arg Lys Gln Met Ala Val Lys Lys
1               5                   10                  15

Tyr Leu

<210> SEQ ID NO 8
<211> LENGTH: 23
<212> TYPE: PRT
<213> ORGANISM: Homo sapiens
<220> FEATURE:
<221> NAME/KEY: MISC_FEATURE
<222> LOCATION: (4)..(5)
<223> OTHER INFORMATION: X is any naturally occurring amino acid residue
<220> FEATURE:
<221> NAME/KEY: MISC_FEATURE
<222> LOCATION: (9)..(13)
<223> OTHER INFORMATION: X is any naturally occurring amino acid residue

<400> SEQUENCE: 8

His Ser Asp Xaa Xaa Phe Thr Asp Xaa Xaa Xaa Xaa Xaa Arg Lys Gln
1               5                   10                  15

Met Ala Val Lys Lys Tyr Leu
            20

<210> SEQ ID NO 9
<211> LENGTH: 23
<212> TYPE: PRT
<213> ORGANISM: Homo sapiens

<400> SEQUENCE: 9

His Ser Asp Ala Val Phe Thr Asp Asn Tyr Thr Arg Leu Arg Lys Gln
1               5                   10                  15

Met Ala Val Lys Lys Tyr Leu
            20

<210> SEQ ID NO 10
<211> LENGTH: 23
<212> TYPE: PRT
<213> ORGANISM: Homo sapiens

<400> SEQUENCE: 10

His Ser Asp Gly Ile Phe Thr Asp Ser Tyr Ser Arg Tyr Arg Lys Gln
1               5                   10                  15

Met Ala Val Lys Lys Tyr Leu
            20

<210> SEQ ID NO 11
<211> LENGTH: 28
<212> TYPE: PRT
<213> ORGANISM: Homo sapiens
```

-continued

```
<220> FEATURE:
<221> NAME/KEY: MISC_FEATURE
<222> LOCATION: (4)..(5)
<223> OTHER INFORMATION: X is any naturally occurring amino acid residue
<220> FEATURE:
<221> NAME/KEY: MISC_FEATURE
<222> LOCATION: (9)..(13)
<223> OTHER INFORMATION: X is any naturally occurring amino acid residue
<220> FEATURE:
<221> NAME/KEY: MISC_FEATURE
<222> LOCATION: (24)..(28)
<223> OTHER INFORMATION: X is any naturally occurring amino acid residue

<400> SEQUENCE: 11

His Ser Asp Xaa Xaa Phe Thr Asp Xaa Xaa Xaa Xaa Xaa Arg Lys Gln
1               5                   10                  15

Met Ala Val Lys Lys Tyr Leu Xaa Xaa Xaa Xaa Xaa
            20                  25

<210> SEQ ID NO 12
<211> LENGTH: 38
<212> TYPE: PRT
<213> ORGANISM: Homo sapiens
<220> FEATURE:
<221> NAME/KEY: MISC_FEATURE
<222> LOCATION: (4)..(5)
<223> OTHER INFORMATION: X is any naturally occurring amino acid residue
<220> FEATURE:
<221> NAME/KEY: MISC_FEATURE
<222> LOCATION: (9)..(13)
<223> OTHER INFORMATION: X is any naturally occurring amino acid residue
<220> FEATURE:
<221> NAME/KEY: MISC_FEATURE
<222> LOCATION: (24)..(38)
<223> OTHER INFORMATION: X is any naturally occurring amino acid residue

<400> SEQUENCE: 12

His Ser Asp Xaa Xaa Phe Thr Asp Xaa Xaa Xaa Xaa Xaa Arg Lys Gln
1               5                   10                  15

Met Ala Val Lys Lys Tyr Leu Xaa Xaa Xaa Xaa Xaa Xaa Xaa Xaa
            20                  25                  30

Xaa Xaa Xaa Xaa Xaa Xaa
        35

<210> SEQ ID NO 13
<211> LENGTH: 3
<212> TYPE: PRT
<213> ORGANISM: Homo sapiens

<400> SEQUENCE: 13

Phe Thr Asp
1

<210> SEQ ID NO 14
<211> LENGTH: 3
<212> TYPE: PRT
<213> ORGANISM: Homo sapiens

<400> SEQUENCE: 14

His Ser Asp
1
```

COMPOUNDS WITH THE BIOLOGICAL ACTIVITY OF VASOACTIVE INTESTINAL PEPTIDE FOR THE TREATMENT OF PULMONARY AND ARTERIOLAR HYPERTENSION

CROSS-REFERENCE TO RELATED APPLICATIONS

This application is a divisional application of U.S. application Ser. No. 10/416,822 filed Oct. 3, 2003 now abandoned which is the national stage entry of PCT application number PCT/EP01/13590 filed Nov. 22, 2001, which in turn stems from European Patent Application No. EP 00125935.7, each of which is incorporated by reference in its entirety.

The present invention relates to peptides which are highly biologically and pharmacologically active as therapeutic drug for the treatment of diseases related to hypertension, especially in medical interventions involving dilatation and remodeling of arterial blood vessels, either in the pulmonary or in the systemic circulation. The peptides which can be used according to the invention for the treatment of said diseases comprise at least one specific highly conservative amino acid residue sequence which seem to play an important role in connection with pulmonary and arteriolar hypertension events. It could be shown that especially the known naturally occurring peptides "vasoactive intestinal peptide (VIP)" and "pituitary adenylate cyclase-activating polypeptide (PACAP)", having these specific sequences are potent drugs which can be successfully used for treatment of primary pulmonary hypertension (PPH), secondary pulmonary hypertension (SPH), and hypertension of the systemic circulation. Furthermore, the present invention discloses pharmaceutical compositions useful for treatment of PPH, SPH, and hypertension of the systemic circulation within said methods.

BACKGROUND OF THE INVENTION

Pulmonary Hypertension:

Primary pulmonary hypertension (PPH) is a fatal disease causing progressive right heart failure within three years after diagnosis. Recently, various pathophysiological changes associated with this disorder, including vasoconstriction, vascular remodelling (i.e. proliferation of both media and intima of the pulmonary resistance vessels), and in situ thrombosis have been characterized (e.g.: D'Alonzo, G. E., Bust, R. J., Ayres, S. M. et al. Survival in patients with primary pulmonary hypertension. Results from a national prospective registry. Ann. Intern. Med. 115, 343-349. Sep. 1, 1991; Palevsky, H. I., Schloo, B. L., Pietra, G. G. et al. Primary pulmonary hypertension. Vascular structure, morphometry, and responsiveness to vasodilator agents. Circulation 80, 1207-1221. 1989; Rubin, L. J. Primary pulmonary hypertension. N. Engl. J. Med. 336, 111-117. Jan. 9, 1997; Wagenvoort, C. A. and Wagenvoort, N. Primary pulmonary hypertension: a pathological study of the lung vessel in 156 clinically diagnosed cases. Circulation 42, 1163-1184. 1970; Wood, P. Pulmonary hypertension with special reference to the vasoconstrictive factor. Br. heart J. 20, 557-570. 1958). Impairment of vascular and endothelial homeostasis is evidenced from a reduced synthesis of prostacyclin ($PGI_2$), increased thromboxane production, decreased formation of nitric oxide and increased synthesis of endothelin-1 (Giaid, A. and Saleh, D. Reduced expression of endothelial nitric oxide synthase in the lungs of patients with pulmonary hypertension. N. Engl. J. Med. 333, 214-221. 1995; Xue, C. and Johns, R. A. Endothelial nitric oxide synthase in the lungs of patients with pulmonary hypertension [letter]. N. Engl. J. Med. 333, 1642-1644. Dec. 14, 1995). The intracellular free calcium concentration of VSMC of pulmonary arteries in PPH has been reported to be elevated. The therapy of pulmonary hypertension is unsatisfactory. Current therapy involves calcium cannel blockers and prostacyclins. Although the vasodilation in numerous tissues, heart and lung tissue included, there is no clinical evidence up to now that VIP or PACAP are effective in the treatment of pulmonary hypertension in humans. The invention describes for the first time the clinical relevance of VIP, PACAP and compounds having the biological activity of VIP or PACAP for the treatment of primary pulmonary hypertension (PPH), secondary pulmonary hypertension (SPH), and arteriolar hypertension associated with PPH.

Arterial Hypertension:

Comparable to the pulmonary circulation, endothelial cells of the systemic circulation release both relaxing and contracting factors that modulate vascular smooth muscle tone and also participate in the pathophysiology of essential hypertension. Endothelium-dependent vasodilation is regulated primarily by nitric oxide but also by an unidentified endothelium-derived hyperpolarizing factor and by prostacyclin. Endothelium-derived contracting factors include endothelin-I, vasoconscrictor prostanoids, angiotensin II and superoxide anions. Under physiological conditions, there is a balanced release of relaxing and contracting factors. The balance can be altered in cardiovascular diseases such as hypertension, atherosclerosis, diabetes and other conditions, thereby contributing to further progression of vascular and end-organ damage. In particular, endothelial dysfunction leading to decreased bioavailability of nitric oxide impairs endothelium-dependent vasodilation in patients with essential hypertension and may also be a determinant for the premature development of atherosclerosis. Different mechanisms of reduced nitric oxide activity have been shown both in hypertensive states and several cardiovascular diseases, and endothelial dysfunction is likely to occur prior to vascular dysfunction.

VIP and PACAP are synthesized in various components of the central nervous system, e.g. specific brain regions like hippocampus and cortex as well as in the pituitary gland and peripheral ganglia. VIP is furthermore secreted by immune cells and by some neoplastic cells (e.g. pancreatic cancer).

Vasoactive Intestinal Peptide (VIP):

VIP is a 28 amino acid peptide consisting of the following amino acid sequence (from N- to C-terminal): His-Ser-Asp-Ala-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn (SEQ ID No. 1).

Healthy individuals exhibit low concentration of VIP (<40 pg/ml serum). VIP is a widely distributed peptide hormone which mediates a variety of physiological responses including gastrointestinal secretion, relaxation of gastrointestinal vascular and respiratory smooth muscle, lipolysis in adipocytes, pituitary hormone secretion, and excitation and hyperthermia after injection into the central nervous system. Under physiologic conditions VIP acts as a neuroendocrine mediator. Some recent findings suggest that VIP also regulates growth and proliferation of normal as well as malignant cells (Hultgardh, Nilsson A., Nilsson, J., Jonzon, B. et al. Growth-inhibitory properties of vasoactive intestinal polypeptide. Regul. Pept. 22, 267-274. 1988). The biological effects are mediated via specific receptors (VIP-R) located on the surface membrane of various cells (Ishihara, T., Shigemoto, R., Mori, K. et al. Functional expression and tissue distribution of a novel receptor for vasoactive intestinal polypeptide. Neuron 8, 811-819. 1992). VIP may exert stimulating and trophic effects on neoplastic cells from neuroblastoma, breast, lung and colon cancer (e.g. Moody et al., Proc. Natl. Acad. Sci. USA, 90, 4345, 1993), inducing its own receptors by feedback mechanisms. In some cases VIP produced dose-dependent stimulation of mitosis (Wollman et al., Brain Res., 624, 339, 1993). VIP and biologically functional analogues and derivatives thereof are shown to have vascular smooth muscle relaxant activity (Maruno, K., Absood, A., and Said, S. I. VIP inhibits basal and histamine-stimulated proliferation of human airway smooth muscle cells. Am. J. Physiol. 268, L1047-L1051, 1995), hair growth activity, apoptosis activity enhanced sustained bronchodilation activity without remarkable cardiovascular side effects, and are effective against disorders or diseases relating to bronchial spasms including asthma, some cases of hypertension, impotence, ischaemia, dry eye and mental disorders, such as Alzheimer's disease (see e.g. WO 9106565, EP 0536741, U.S. Pat. No. 3,880,826, EP 0204447, EP 0405242, WO 9527496, EP 0463450, EP 0613904, EP 0663406, WO 9735561, EP 0620008).

VIP receptor has been detected on airway epithelium of the trachea and the bronchioles. It is also expressed in macrophages surrounding capillaries, in connective tissue of trachea and bronchi, in alveolar walls, and in the subintima of pulmonary veins and pulmonary arteries.

Pepidergic nerve fibers are considered the source of VIP in the lungs (e.g.: Dey, R. D., Shannon-WA, Jr, and Said, S. I. Localization of VIP-immunoreactive nerves in airways and pulmonary vessels of dogs, cat, and human subjects. Cell and Tissue Research 220, 231-238. 1981; Said, S. I. Vasoactive intestinal polypeptide (VIP) in asthma. Ann. N.Y. Acad. Sci. 629, 305-318. 1991). VIP decreases the resistance in the pulmonary vascular system (e.g.: Hamasaki, Y., Mojarad, M., and Said, S. I. Relaxant action of VIP on cat pulmonary artery: comparison with acetylcholine, isoproterenol, and PGE1. J. Appl. Physiol. 54, 1607-1611. 1983; Iwabuchi, S., Ono, S., Tanita, T. et al. Vasoactive intestinal peptide causes nitric oxide-dependent pulmonary vasodilation in isolated rat lung. Respiration 64, 54-58. 1997; Saga, T. and Said, S. I. Vasoactive intestinal peptide relaxes isolated strips of human bronchus, pulmonary artery, and lung parenchyma. Trans. Assoc. Am. Physicians. 97, 304-310. 1984). Further studies show a high rate of VIP-R expression in the lung which is reflected in a high uptake of radiolabeled VIP in the lung of PPH patients who were injected 99 mTc-VIP (e.g.: Raderer, M., Kurtaran, A., Hejna, M. et al. 123I-labelled vasoactive intestinal peptide receptor scintigraphy in patients with colorectal cancer. Br. J. Cancer 78, 1-5. 1998; Raderer, M., Kurtaran, A., Yang, Q. et al. Iodine-123-vasoactive intestinal peptide receptor scanning in patients with pancreatic cancer. J. Nucl. Med. 39, 1570-1575. 1998; Raderer, M., Kurtaran, A., Leimer, M. et al. Value of peptide receptor scintigraphy using (123)I-vasoactive intestinal peptide and (111)In-DTPA-D-Phe1-octreotide in 194 carcinoid patients: Vienna University Experience, 1993 to 1998. J. Clin. Oncol. 18, 1331-1336. 2000; Virgolini, I., Kurtaran, A., Raderer, M. et al. Vasoactive intestinal peptide receptor scintigraphy. J. Nucl. Med. 36, 1732-1739. 1995).

Pituitary Adenylate Cyclase-Activating Polypeptide (PACAP):

PACAP is a neuropeptide isolated from the ovine hypothalamus consisting of the following 38 amino acid residues containing sequence (from N- to C-terminal): His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys-Asn-Lys (SEQ ID No. 2).

Two forms of the peptide have been identified: PACAP-38 and the C-terminally truncated PACAP-27. PACAP-27 that shares 68 percent homology with VIP has the following sequence (from N- to C-terminal): His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu (SEQ ID No. 3)

PACAP is very potent in stimulating adenylate cyclase and thus increasing adenosine 3,5-cyclic monophosphate (cAMP) in various cells. The compound functions as a hypothalamic hormone, neurotransmitter, neuromodulator, vasodilator, and neurotrophic factor. The major regulatory role of PACAP in pituitary cells appears to be the regulation of gene expression of pituitary hormones and/or regulatory proteins that control growth and differentiation of the pituitary glandular cells. These effects appear to be exhibited directly and indirectly through a paracrine or autocrine action. PACAP plays an important role in the endocrine system as a potent secretagogue for adrenaline from the adrenal medulla. The compound also stimulates the release of insulin. The stage-specific expression of PACAP in testicular germ cells during spermatogenesis suggests its regulatory role in the maturation of germ cells. In the ovary, PACAP is transiently expressed in the granulosa cells of the preovulatory follicles and appears to be involved in the LH-induced cellular events in the ovary, including prevention of follicular apoptosis. In the central nervous system, PACAP acts as a neurotransmitter or a neuromodulator. More important, PACAP is a neurotrophic factor that may play a significant role during the development of the brain. In the adult brain, PACAP appears to function as a neuroprotective factor that attenuates the neuronal damage resulting from various insults. PACAP is widely distributed in the brain and peripheral organs, notably in the endocrine pancreas, gonads, and respiratory and urogenital tracts. Two types of PACAP binding sites have been characterized. Type I binding sites exhibit a high affinity for PACAP (and a much lower affinity for VIP), whereas type II binding sites have similar affinity for PACAP and VIP. Molecular cloning of PACAP receptors has shown the existence of three distinct receptor subtypes. These are the PACAP-specific PAC1 receptor, which is coupled to several transduction systems, and the two PACAP/VIP-indifferent VPAC1 and VPAC2 receptors, which are primarily coupled to adenylyl cyclase. PAC1 receptors are particularly abundant in the brain and pituitary and adrenal glands whereas VPAC receptors are expressed mainly in the lung, liver, and testes.

Vascular Tone:

The vascular tone is regulated by a complex network of vasoactive effector substances produced either locally in the endothelium, in vascular smooth muscle cells (VSMC), in extrinsic and intrinsic nerves, and by the vascular blood flow itself. In addition to sympatic and parasympatic nervous pathways, neuropeptides from the peripheral nervous system also appear to play an important role in the regulation of vascular tone. One of the most important pathways for the regulation of vascular tone is the production of nitric oxide by the endothelial nitric oxide synthetase (ecnos, NOS III).

SUMMARY OF THE INVENTION

It is object of the present invention to provide novel use of known compounds as well as novel compounds, which are useful for the prevention and/or treatment of PPH, SPH, and hypertension of the systemic circulation and methods wherein said compounds are used.

Surprisingly it was found that peptides or polypeptides comprising the highly conservative decapeptide sequence Arg-Lys-Gln-Met-Ala-Val-Lys-Lys-Tyr-Leu (SEQ ID NO: 4) show highly efficacy when administered to patients suffering from hypertension symptoms and disorders. Compounds comprising this sequence and having totally 10-60, preferably 10-38, more preferably 10-28 or 10-23 amino acid residues have very similar or identical biological function as VIP or PACAP which also comprise said highly conservative sequence. It is another result of the present invention that VIP, PACUP and also its truncated forms, for example PACAP-27, are also highly active compounds for the prophylaxis and treatment of PPH, SPH, and hypertension of the systemic circulation by inhibition and/or regulation of cellular processes underlying the said diseases in humans.

Generally, it was found that VIP- and PACAP-like peptides and polypeptides can show the above-described therapeutic function and efficacy which have the following amino acid sequence: $(A)_n$-Arg-Lys-Gln-Met-Ala-Val-Lys-Lys-Tyr-Leu-$(B)_m$,
[that is, $(A)_n$-(SEQ ID NO:4)-$(B)_m$]
wherein A, B is any natural occurring amino acid residue, A and B are independently from each other; and n, m is an integer having values from 0-25; n and m being independently from each other. The value of m is preferably 4-18, more preferably 5-15, and most preferably 10-15.

Polypeptides or peptides, wherein $(A)_n$ (if n>2) comprises the tripeptide sequences His-Ser-Asp (SEQ ID NO: 14) and/or Phe-Thr-Asp (SEQ ID NO: 13) in N-terminal direction near by (1-10 amino acid residues) above-specified decapeptide sequence have an enhanced activity.

Thus polypeptides, wherein
(A), (if n>2) has the meaning of $(X)_o$-Phe-Thr-Asp-$(Y)_p$
[that is, $(X)_o$-(SEQ ID NO: 13)-$(Y)_p$] and
$(X)_o$ (if o>2) has the meaning of $(X')_q$-His-Ser-Asp-$(X'')_r$
[that is, $(X')_q$-(SEQ ID NO:14)-$(X'')_r$]
wherein X, Y, X', X'' is any natural occurring amino acid residue; and o, p, is an integer having values from 0-11, and r, q is an integer having values from 0-4, show especially improved efficacy. Preferred values of o and p are 0-8, more preferably 1-5. Preferred values of r are 0-2.

Preferred examples falling under the generic formula are
His-Ser-Asp-Ala-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn (VIP) (SEQ ID NO: 1);
His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys-Asn-Lys (PACAP-38) (SEQ ID NO: 2);
His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu (PACAP-27) (SEQ ID NO: 3);

This invention discloses also novel compounds falling under the above-specified formula:

$(A)_n$-Arg-Lys-Gln-Met-Ala-Val-Lys-Lys-Tyr-Leu-$(B)_m$ [that is, $(A)_n$-(SEQ ID NO: 4)-$(B)_m$]

wherein A, B is any natural occurring amino acid residue, A and B are independently from each other; and n, m is an integer having values from 0-25, n and m being independently from each other, provided that VIP, PACAP and PACAP-27 (truncated PACAP) is excluded.

Preferred examples of these novel polypeptides are:
(i) Arg-Lys-Gln-Met-Ala-Val-Lys-Lys-Tyr-Leu (SEQ ID NO: 4);
(ii) Phe-Thr-Asp-$X^1$-$X^2$-$X^3$-$X^4$-$X^5$-Arg-Lys-Gln-Met-Ala-Val-Lys-Lys-Tyr-Leu-Asn-Ser-Ile-Leu-Asn (SEQ ID NO: 5);
(iii) Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn (SEQ ID NO: 6);
(iv) Phe-Thr-Asp-Ser-Tyr-Ser-Arg-Tyr-Arg-Lys-Gln-Met-Ala-Val-Lys-Lys-Tyr-Leu (SEQ ID NO: 7);
(v) His-Ser-Asp-$X^1$-$X^2$-Phe-Thr-Asp-$X^3$-$X^4$-$X^5$-$X^6$-$X^7$-Arg-Lys-Gln-Met-Ala-Val-Lys-Lys-Tyr-Leu (SEQ ID NO: 8);
(vi) His-Ser-Asp-Ala-Val-Phe-Thr-Asp-Asn-Tyr-Thr-Arg-Leu-Arg-Lys-Gln-Met-Ala-Val-Lys-Lys-Tyr-Leu (SEQ ID NO: 9);
(vi) His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu (SEQ ID NO: 10);
(vii) His-Ser-Asp-$X^1$-$X^2$-Phe-Thr-Asp-$X^3$-$X^4$-$X^5$-$X^6$-$X^7$-Arg-Lys-Gln-Met-Ala-Val-Lys-Lys-Tyr-Leu-$X^8$-$X^9$-$X^{11}$(-$X^{12}$) (SEQ ID NO: 11);
(viii) His-Ser-Asp-$X^1$-$X^2$-Phe-Thr-Asp-$X^3$-$X^4$-$X^5$-$X^6$-$X^7$-Arg-Lys-Gln-Met-Ala-Val-Lys-Lys-Tyr-Leu-$X^8$-$X^9$-$X^{10}$-$X^{11}$-$X^{12}$-$X^{13}$-$X^{14}$-$X^{15}$-$X^{16}$-$X^{17}$-$X^{18}$-$X^{19}$-$X^{20}$-$X^{21}$-$X^{22}$ (SEQ ID NO: 12);
wherein $X^1$-$X^{22}$ is any naturally occurring amino acid residue.

To sum up, it is an object of this invention to provide the following topics:

A use and a method for treatment of a disease or a disorder correlated directly or indirectly with hypertension symptoms in human lung and/or arterial tissue comprising administering to a patient a compound having the biological activity of vasoactive intestinal peptide (VIP) or pituitary adenylate cyclase-activating polypeptide (PACAP); preferably these compounds are peptides or polypeptides comprising the highly conservative sequence Arg-Lys-Gln-Met-Ala-Val-Lys-Lys-Tyr-Leu (SEQ ID NO: 4), more preferably, they comprise additionally the sequences His-Ser-Asp (SEQ ID NO: 14) and/or Phe-Thr-Asp (SEQ ID NO: 13).

A use and a method for reducing the vessel tone of human pulmonary arterial rings comprising administering to a patient a compound having the biological function of above-specified peptides or polypeptides, preferably VIP, PACKAP and truncated PACKUP.

A use and a method for reducing the intracellular free calcium concentration in human vascular smooth muscle cells (VSMC) comprising administering to a patient a compound having the biological function of above-specified peptides or polypeptides, preferably VIP, PACKAP and truncated PACKUP.

A use and a method for reducing the proliferation of vascular smooth muscle cells (VSMC) of human pulmonary arterial vessels comprising administering to a patient a compound having the biological function of above-specified peptides or polypeptides, preferably VIP, PACKAP and truncated PACKUP.

A use and a method as defined above, wherein the disease is primary pulmonary hypertension (PPH).

A use and a method as defined above, wherein said disease is chronic obstructive pulmonary disease (COPD).

A use and a method as defined above, wherein the disease is secondary pulmonary hypertension (SPH).

A use and method, wherein said disease is arteriolar hypertension.

A use and method, wherein said arteriolar hypertension is associated with PPH.

A use and a method, wherein said disease is heart failure associated with PPH.

A corresponding use and method, wherein the pulmonary arterial pressure is reduced to more than 10%, preferably more than 20%, most preferably between 10 and 30%, after administration of said peptides and/or polypeptides.

A corresponding use and a method, wherein the diastolic blood pressure is reduced to 5-25%, preferably to 10-20%,

DETAILED DESCRIPTION

Suitable compounds which have the therapeutic effect according to the invention, are compounds which have the same, but also reduced or enhanced, biological activity of VIP or PACAP. Preferred compounds according to the invention have the same or an enhanced biological activity. All compounds falling under this group comprise the sequence Arg-Lys-Gln-Met-Ala-Val-Lys-Lys-Tyr-Leu (SEQ ID NO: 4).

The invention includes also derivatives of the disclosed peptides and polypeptides having the same biological activity.

The term "same biological activity" means the biological, physiological or therapeutic activity or functionality compared with the relevant properties of said peptides and polypeptides, preferably VIP or PACAP.

The term "derivative" means a peptide compound which derives more or less direct from the corresponding peptide, such as VIP or PACKUP as such, and is altered by some additions, deletions, mutations or modifications without altering the biological properties of the parent peptide. Suitable VIP derivatives are, for example, disclosed in WO 8905857, WO 9106565, EP 0663406 and WO 9729126 (Fmoc protected VIP). The term includes also conjugates of peptides and polypeptides according to the invention which consist of the parent peptide or polypeptide coupled to lipophilic entities, such as liposomes. VIP-liposome products are, for example, disclosed in WO 9527496 or WO 9735561, and have improved properties with respect to bioavailability and proteolytic degradation. Furthermore, the term includes also fragments, slightly modified fragments including truncated forms.

The term "analogue" means a compound which may have a different structure and composition compared with the polypeptides and peptides according to the invention, preferably VIP, however without having altered biological properties. VIP analogues may be natural or synthetic peptides but also non-peptides. Preferably, VIP analogues according to the invention are peptides. Examples for known VIP analogues are disclosed in EP 0325044 (cyclic peptides), EP 0225020 (linear peptides), EP 0536741 (cyclic VIP modifications), EP 0405242, EP 0184309 and EP 0613904. The term includes also VIP or PACAP homologues, which are not VIP or PACAP but show great structural similarity to VIP. Such a VIP homologue according to the invention is PACAP itself and its truncated form PACAP-27. The term also includes such homologues which could form, like VIP, amphipathic helices. Preferred VIP/PACAP homologues are peptides that comprise one or more consensus sequences. Examples are peptide histidine isoleucine (PHI), peptide histidine methionine (PHM), human growth hormone releasing factor (GRF), pituitary adenylate cyclase activating peptide (PACAP), secretin and glucagon.

The term "stabilized form" means a derivative or analogue wherein the parent peptide was altered in order get more stability and increased half-life in blood and serum. Such stabilized forms are preferred if the polypeptide is fragmented by enzyme activity. Possible stabilized forms are cyclic peptides or polypeptides like cyclic VIP or cyclic PACAP, fusion proteins, preferably Fc-fusion proteins or pegylated polypeptides, for example pegylated VIP or PACAP. Methods for manufacturing such polypeptides are well known in the art. Polypeptides and proteins may be protected against proteolysis by the attachment of chemical moieties. Such attachment may effectively block the proteolytic enzyme from physical contact with the protein backbone itself, and thus prevent degradation. Polyethylene glycol is one such chemical moiety which has been shown to protect against proteolysis (Sada, et al., J. Fermentation Bioengineering 71: 137-139, 1991). In addition to protection against proteolytic cleavage, chemical modification of biologically active proteins has been found to provide additional advantages under certain circumstances, such as increasing the stability and circulation time of the therapeutic protein and decreasing immunogenicity. (U.S. Pat. No. 4,179,337; Abuchowski et al., Enzymes as Drugs; J. S. Holcerberg and J. Roberts, eds. pp. 367-383, 1981; Francis, *Focus on Growth Factors* 3: 4-10; EP 0 401 384). The addition of polyethylene glycol increases stability of the peptides and polypeptides of this invention at physiological pH as compared to non-pegylated compounds. The pegylated polypeptide/protein is also stabilized with regard to salts.

The term "fusion protein" means a compound, especially a stabilized form, consisting of a polypeptide according to the invention, preferably VIP or a VIP derivative or analogue, such as PACAP, which is fused to another peptide or protein. Such a protein is preferably an immunglobulin molecule, more preferably a fragment thereof, most preferably a Fc portion of an IgG molecule, preferably an IgG1. A Fc-VIP fusion protein is described in WO 200024278 and shows an improved half-life in serum and blood. A further example is Fc-PACAP and FC-PACAP-27.

The compound according to the invention can be used as medicament or as diagnostic means to evaluate pathological conditions in an individual.

The term "individual" preferably refers to mammals, especially humans. The compound is used in a pharmaceutical composition and formulations, comprising, as a rule, a pharmaceutically acceptable carrier, excipient or diluents. Techniques for the formulation and administration of the compounds of the present invention may be found in "Remington's Pharmaceutical Sciences" Mack Publishing Co., Easton Pa.

As used herein, the term "pharmaceutically acceptable carrier" means an inert, non toxic solid or liquid filler, diluent or encapsulating material, not reacting adversely with the active compound or with the patient, or any other formulation such as tablets, pills, dragees, capsules, gels, syrups, slurries, suspensions and the like. Suitable, preferably liquid carriers are well known in the art such as sterile water, saline, aqueous dextrose, sugar solutions, ethanol, glycols and oils, including those of petroleum, animal, vegetable, or synthetic origin, for example, peanut oil, soybean oil and mineral oil.

The formulations according to the invention may be administered as unit doses containing conventional non-toxic pharmaceutically acceptable carriers, diluents, adjuvants and vehicles which are typical for parenteral administration.

The term "parenteral" includes herein subcutaneous, intravenous, intra-articular and intratracheal injection and infusion techniques. Parenteral compositions and combinations are most preferably administered intravenously either in a bolus form or as a constant fusion according to known procedures.

Also other administrations such as oral administration or administration by inhalation or nasal spray are suitable.

Tablets and capsules for oral administration contain conventional excipients such as binding agents, fillers, diluents, tableting agents, lubricants, disintegrants, and wetting agents. The tablets may be coated according to methods well known in the art.

For inhalations the compound according to the invention is preferably brought in an aerosol form. Aerosols and techniques to make them are well known in the art. Aerosols applicable by inhalers containing a peptide or polypeptide of the invention, for example, VIP or PACAP are preferred if direct pulmonary symptoms have to be treated.

Unit doses according to the invention may contain daily required amounts of the compound according to the invention, or sub-multiples thereof to make up the desired dose. The optimum therapeutically acceptable dosage and dose rate for a given patient (mammals, including humans) depends on a variety of factors, such as the activity of the specific active material employed, the age, body weight, general health, sex, diet, time and route of administration, rate of clearance, enzyme activity, the object of the treatment, i.e., therapy or prophylaxis and the nature of the disease to be treated. Therefore, in compositions and combinations in a treated patient (in vivo) a pharmaceutical effective daily dose of the compound of this invention is between about 5 ng and 200 µg/kg body weight, preferably between 20 ng and 20 µg/kg body weight.

Combination Therapy

The compounds of the invention may be administered to a subject in need thereof, e.g. a human patient, by itself or in pharmaceutical compositions where they are mixed with suitable carriers or excepients at doses which are sufficient for at least the inhibition of the diseases' progression. Therapeutically effective doses may be administered alone or as adjunctive therapy in combination with other pharmaceutically effective compounds, such as compounds with other vasodilator drugs, e.g. Epoprostenol, Iloprost, Uniprost; calcium channel-blocking agents, e.g. diltiazem; phosphodiesterase isoenzyme inhibitors, e.g. Sildenafil, immunosuppressive drugs, e.g. glucocorticosteroids, e.g. prednisolone, antimicrobial agents, e.g. antibiotics, inotropic and/or vasodilatory effective agents, e.g. beta-adrenergic receptor blocking agents and angiotensin receptor antagonists or angiotensin converting enzyme-inhibitors, e.g. ramipril, lipid lowering and antiproliferative drugs, e.g. atorvastatin, endothelin receptor antagonists, e.g. Bosentan, Altrasentan, Sitaxsentan, Enrasentan, BMS 193884, Darusentan, TBC 3711, BSF 208075, BSF 302146, SPP 301, or other antiproliferative compounds, e.g. D-24851, Imatinib mesylate, guanyl hydrazone CNI-1493. This invention also relates to the combination of the compounds described in the present invention with at least one of the above mentioned drugs.

It is likely that the therapy with the compounds of the invention, alone or in combination with the above mentioned substances, may lower existing but undesired drug effects in a subject in need of those drugs.

Surprisingly, it was found that the peptides and polypeptides as defined above and in the claims, above all VIP and PACAP, have beneficial effects in the treatment of pulmonary and systemic hypertension as demonstrated in the following examples. These data show a dramatic improvement for the treatment of as yet not sufficiently treatable diseases. It is a benefit of this invention that all tested polypeptides comprising the highly conservative decapeptide sequence as depicted in above are efficacious.

SHORT DESCRIPTION OF THE FIGURES

FIG. 1: VIP serum concentration of different patients as detected by radioimmunoassay. Column (a): healthy subjects (n=3), column (b): PPH (n=3).

FIG. 2: (2a): Immunohistochemical characterization of VIP protein (B) and VIP receptor (VIP-R1) (A) in lung tissue specimens of PPH patients (b) and control (a). Note the lack of VIP protein in PPH contrary to the immunostaining in normals (arrows). Reversely, VIP receptor expression is apparently upregulated in PPH compared controls.

(2b): VIP positive fibers per vessel (y-axis) in VIP-reactive fibers (A) and VIP-R on PVSMC (B). Controls (a), PPH patients (b).

FIG. 3: Transcription of VIP-R mRNA as evidenced from Northern blotting in VSMC prepared from the pulmonary arteries of PPH patients and controls.

FIG. 4: Binding of 99 mTc-VIP to isolated VSMC prepared from pulmonary arteries of PPH patients (4b) and control patients (4a). Note the increased specific binding (Bmax=0.9 pm per mg protein) and binding affinity in PPH (Kd=1.6 pM), vs. Bmax=0.6 pm per mg protein, Kd=42 pM of control.

Figure 5A:
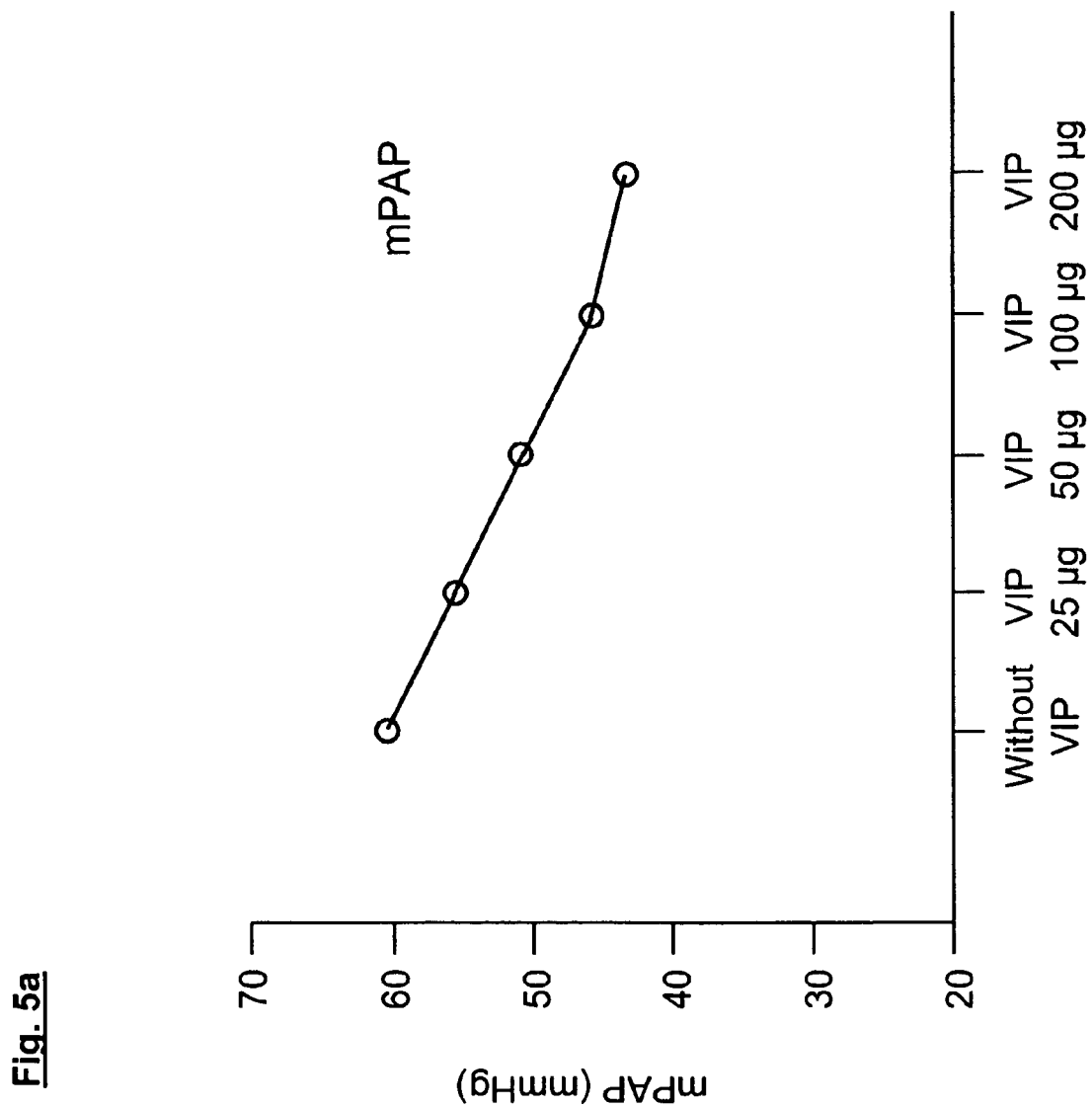
Figure 5B:
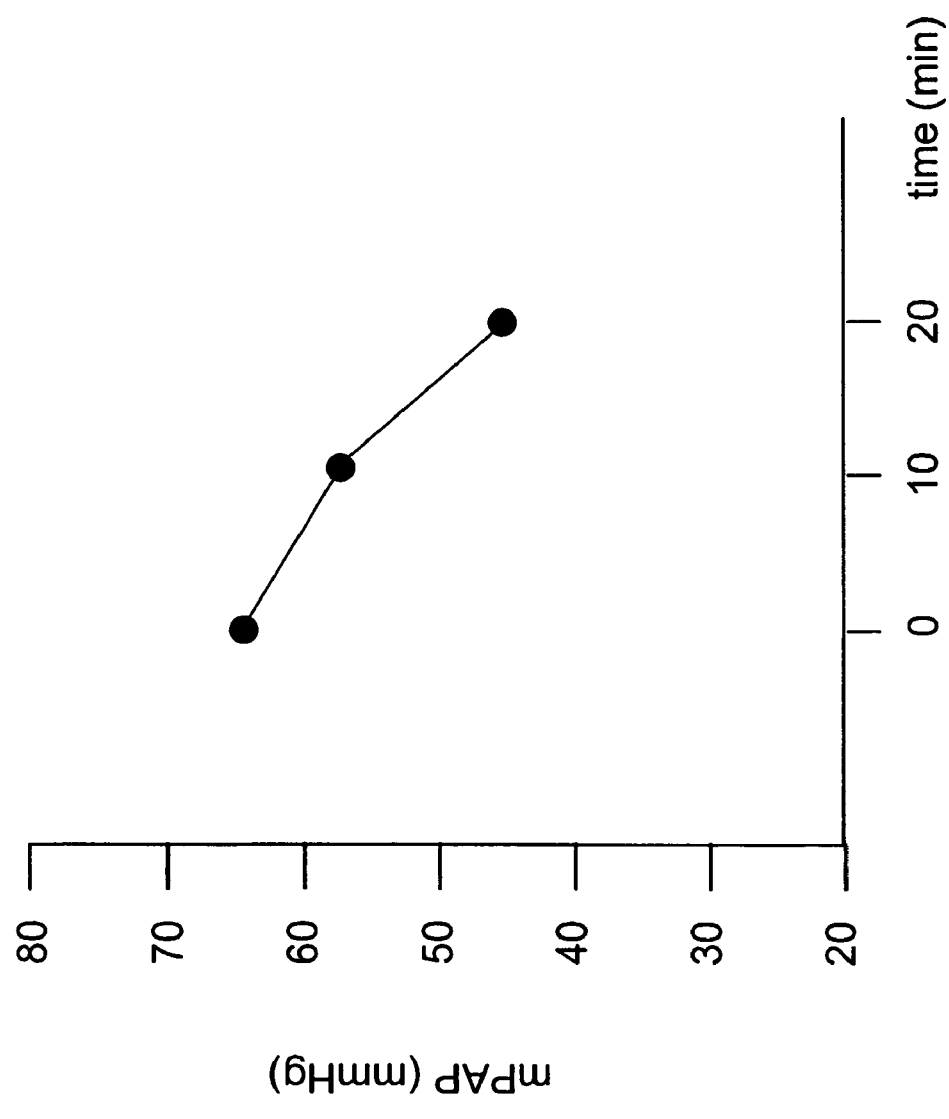

FIG. 5: (5a): Dose-dependent amelioration of pulmonary hemodynamics by inhaled VIP of different doses in a patient with PPH (Y-axis: mean pulmonary arterial pressure (mPAP); (5b): Time dependant decrease of mean pulmonary arterial pressure (mPAP) of PPH in a patient after inhalation of VIP (100 µg in 3 ml NaCl 0.9%).

Figure 6:
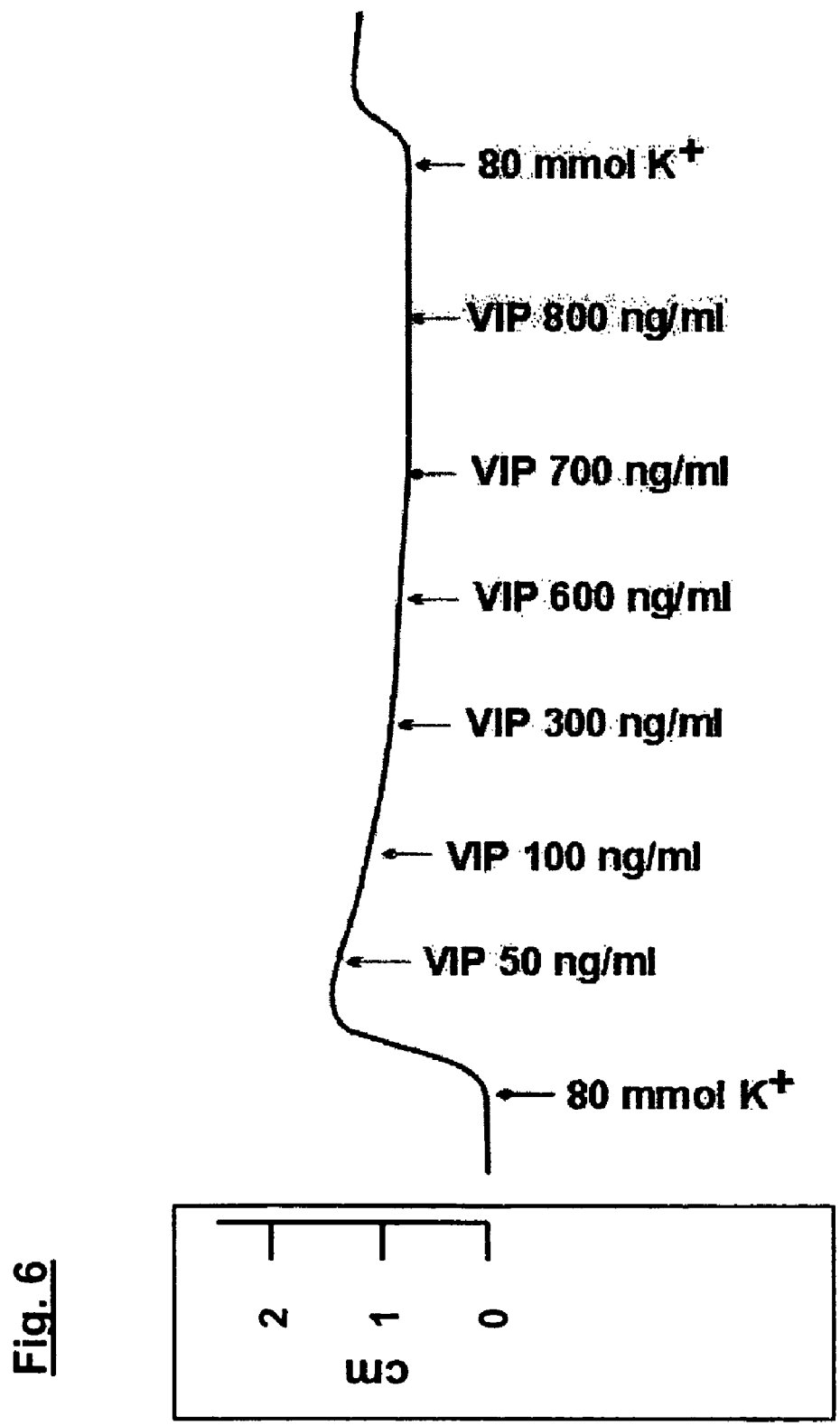

FIG. 6: Vasodilatory effect of VIP on human pulmonary arterial rings. Arteries of patients subjected to thorax surgery were surgically removed and tested in vitro under standardized procedures for their vascular tone. After an increase of vascular tone by addition of 80 mmol $K^+$, the addition of VIP, at increasing concentrations, results in a continuous decrease of the vessel tone.

Figure 7:
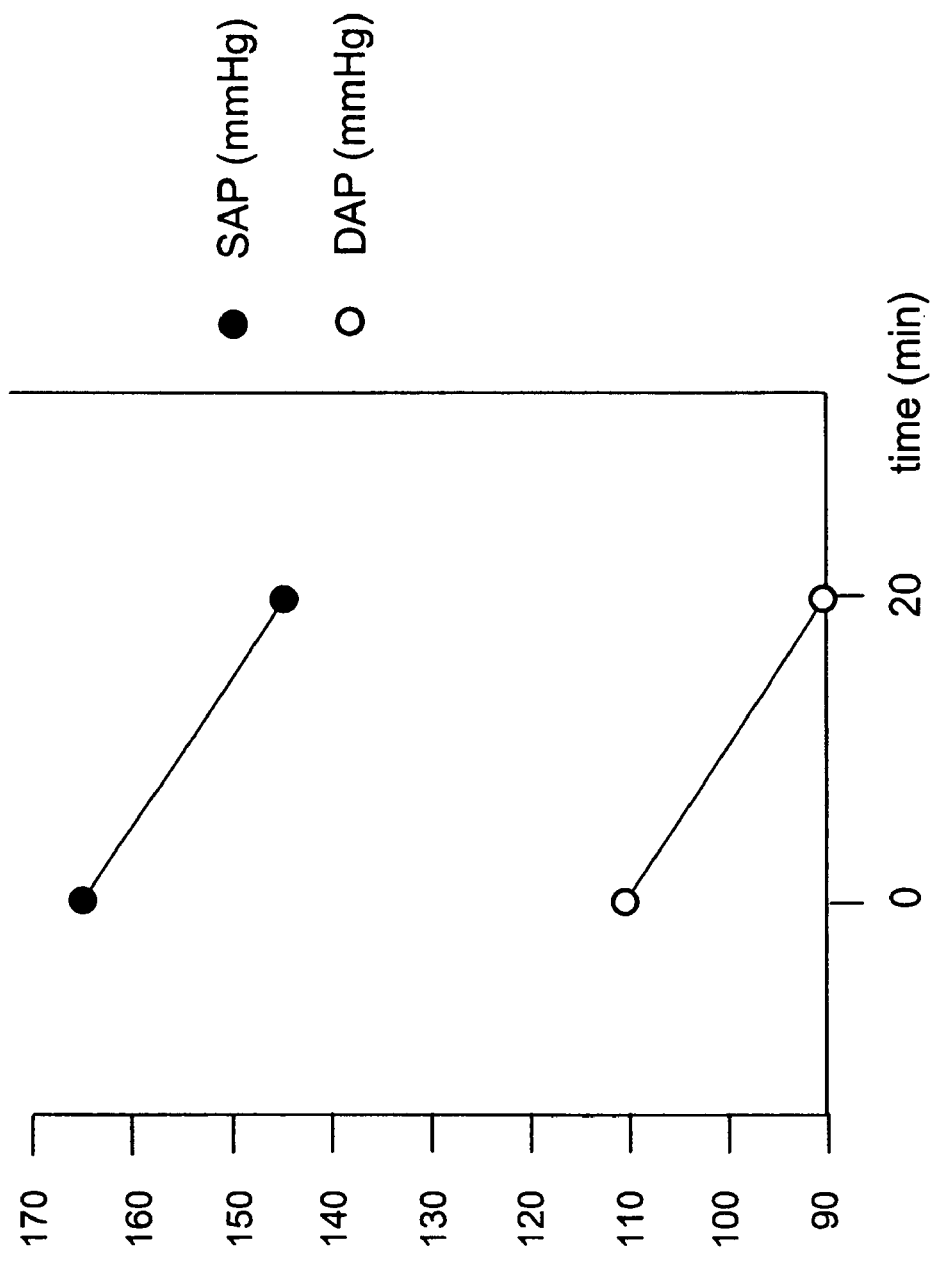

FIG. 7: The effect of VIP on systolic and diastolic blood pressure in a patient with essential hypertension after intravenous injection. The patient received VIP at 20 ng/kg/b.w./min. Blood pressure was measured intraarterially. Y-axis: pressure (mmHg), x-axis: time (min).

Figure 8:
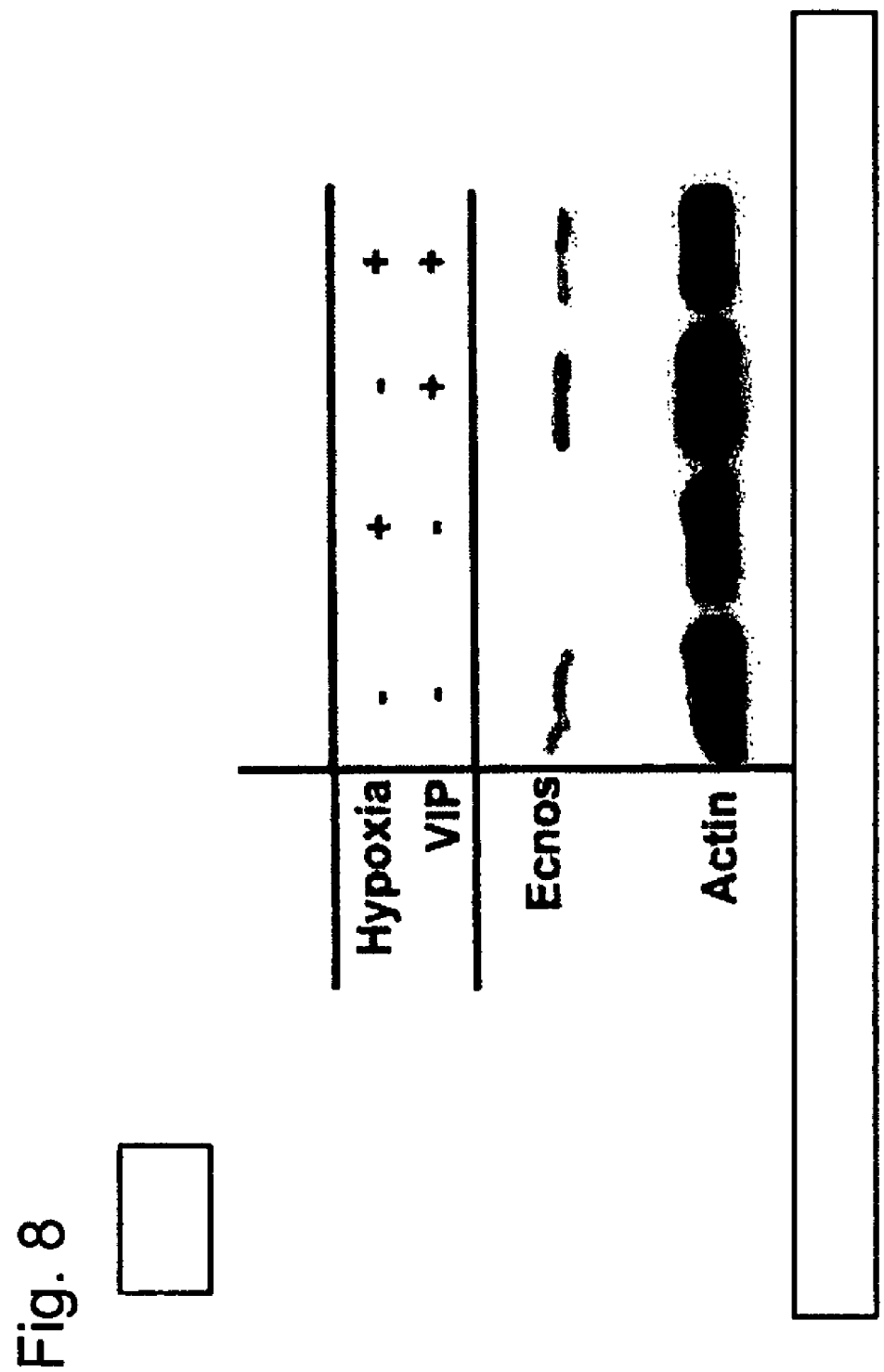

FIG. 8: Nitric oxide synthetase (ecnos) expression in endothelial cells prepared from pulmonary arteries of control subjects after 96 hours of incubation. Cells were incubated with VIP ($10^{-7}$ M) under normoxic (−) and hypoxic (+) conditions for various times. Western blots reveal constitutive expression under normoxic conditions without VIP. Under hypoxic conditions in the absence of VIP the expression of ecnos is completely downregulated. In contrary, the addition of VIP leads to increased expression of ecnos above constitutional level both under normoxic and hypoxic condition.

Figure 9:
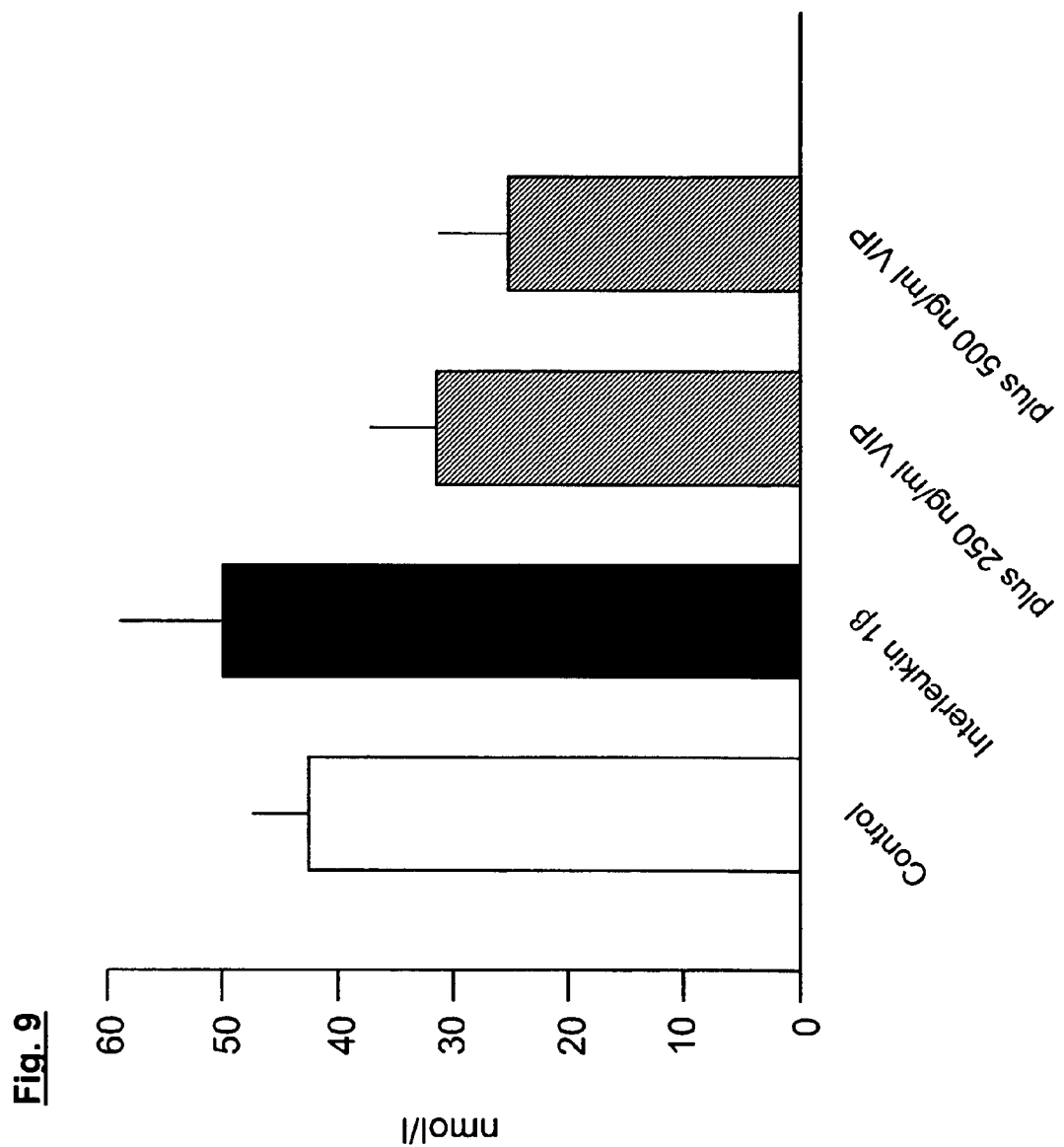

FIG. 9: The effect of VIP on the interleukin1-b induced elevation of intracellular free calcium concentration in VSMC prepared from pulmonary arteries. Ordinate-Ca2+ (nmol). 1-basal concentration; 2-interleukin1-b; 3-interleukin1-b plus VIP 250 ng/ml and 4-VIP 500 ng/ml intracellular calcium concentration during incubation with VIP; Ca 2+ was determined by fura-2 method.

Figure 10:
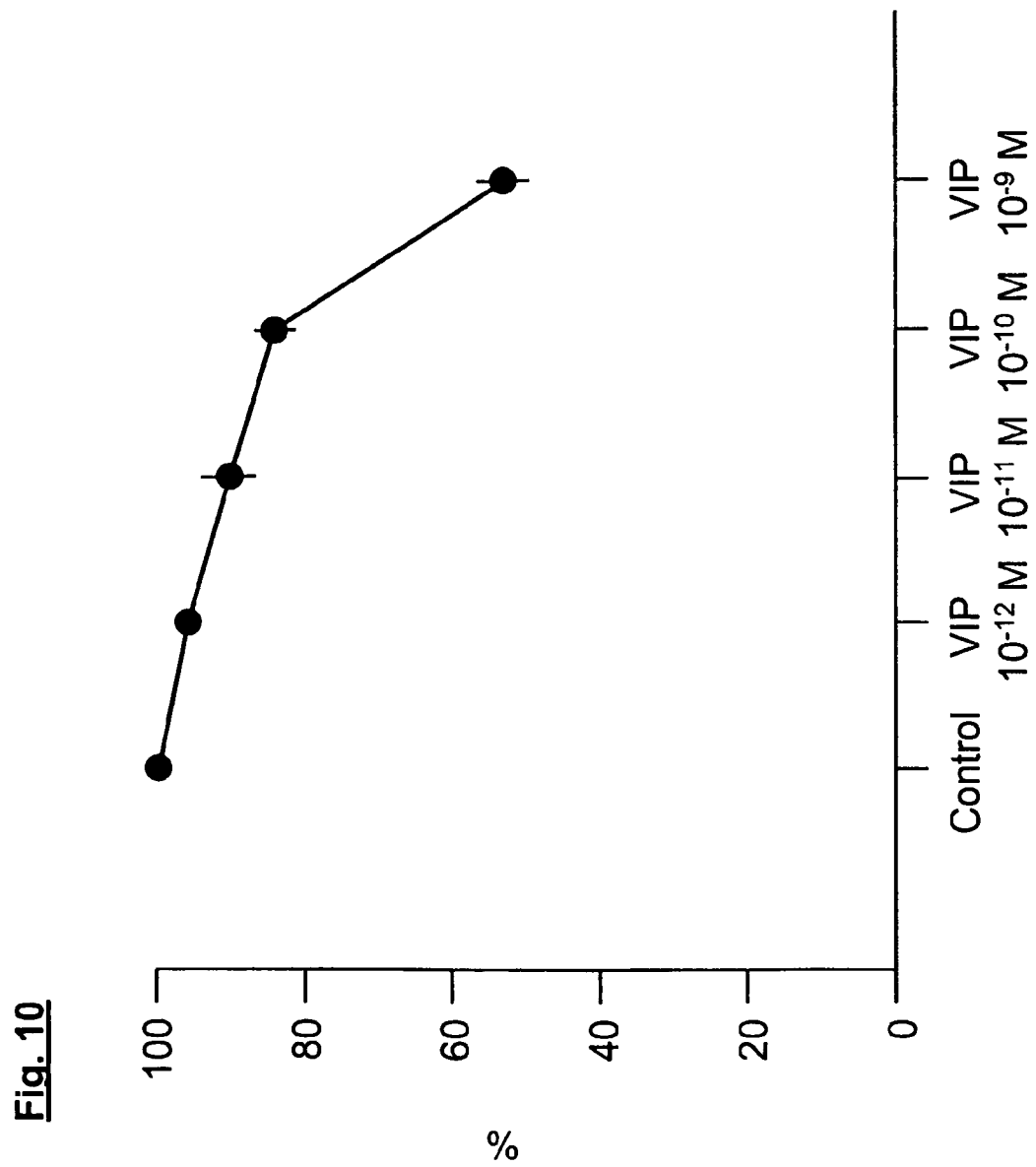

FIG. 10: The effect of VIP on the proliferation of VSMC from pulmonary arterial vessel. Ordinate-proliferation as percent of control. 1-without VIP; 2-$10^{-12}$M VIP; 3-$10^{-11}$M VIP; 4-$10^{-10}$M VIP; 5-$10^{-9}$M VIP.

In Vitro Experimental Data Supporting Clinical Findings

Figure 2A:
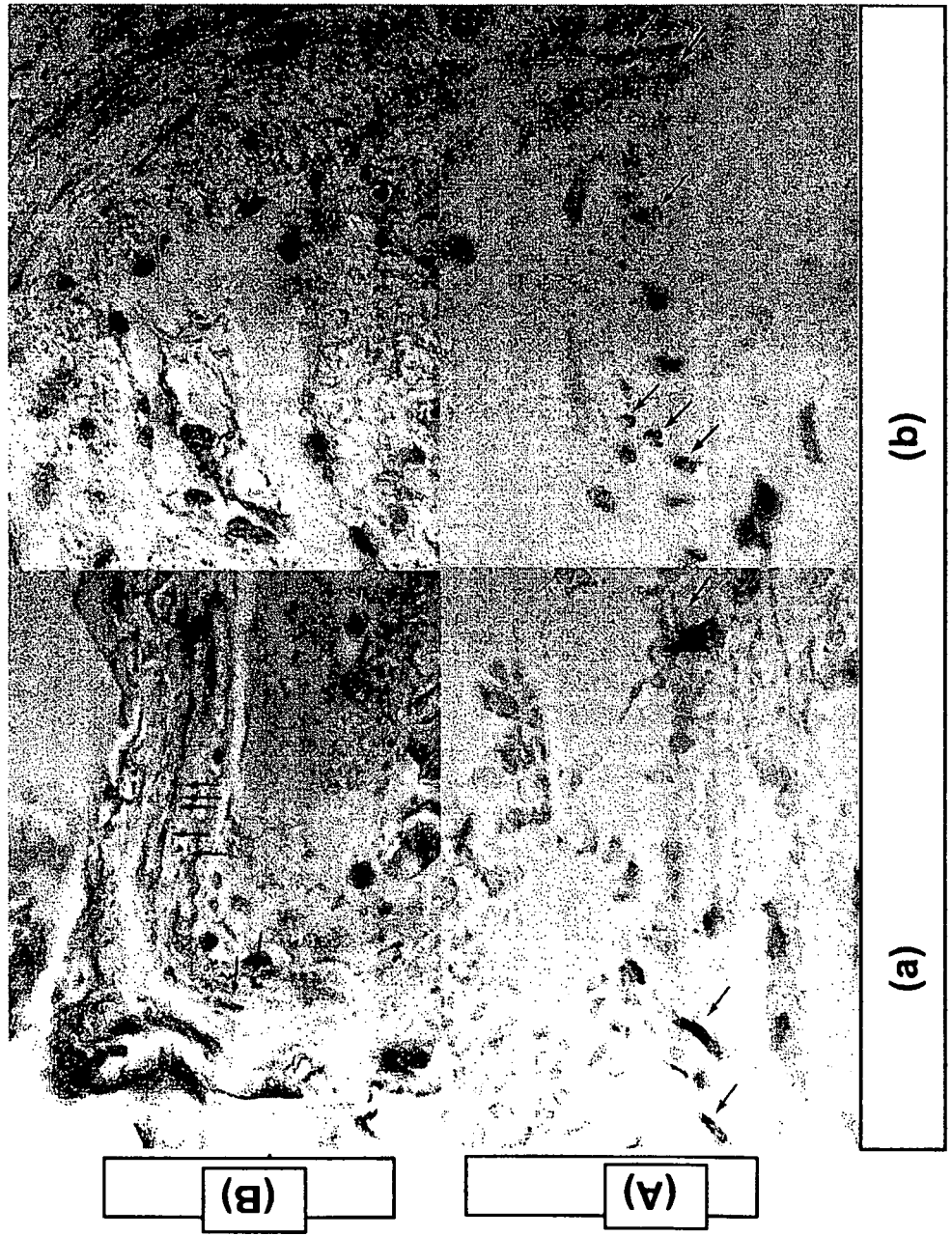
Figure 4B:
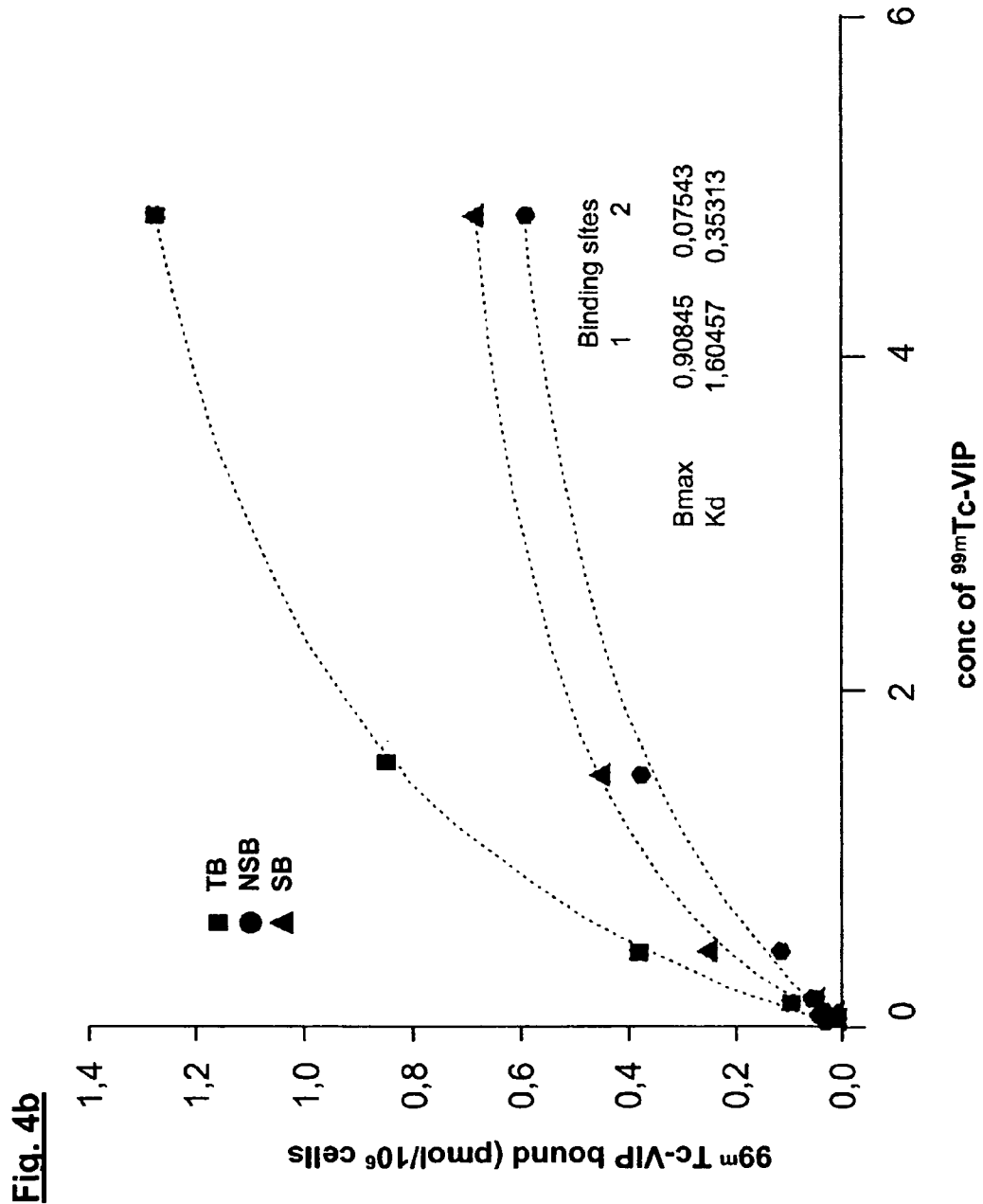

The serum concentration of VIP shows profound differences between PPH-patients, other patients or healthy controls (FIG. 1). Immunohistochemical analysis of the expression of VIP-R reveals the intimate connection between its expression and the state of the disease (FIGS. 2a and 2b). While VIP-R mRNA accumulation is easily detectable PPH, only low levels of VIP-R mRNA accumulation can be detected in healthy controls (FIG. 3). Analogously an increased receptor binding activity for VIP is seen in primary cultures of pulmonary artery vascular smooth muscle cells (PaVSMC) prepared from pulmonary resistance vessels of PPH patients compared to healthy subjects (FIGS. 4a and 4b). FIG. 8 shows the effect of VIP on the expression of ecnos (NOS III) in human endothelial cells of pulmonary arteries under normoxic and hypoxic conditions, a situation by which ecnos is usually decreased. Pharmacologically, nitric oxide induces vasodilatation by lowering the intracellular free calcium concentration of PaVSMC. Analogously, the molecular mechanism of VIP action apparently involves a decrease of the intracellular free calcium concentration in VSMC, as illustrated in FIG. 9. Moreover, VIP inhibits the proliferation of PaVSMC (FIG. 10). The vasodilatory effect of VIP on arterial rings of human pulmonary arteries is shown in FIG. 6.

Example 1

A patient with severe PPH was under therapy with diltiazem, furosemid and an anticoagulant. Right heart catheterisation (Swan-Ganz, Baxter, Irvine, Calif., USA) was performed to measure mean pulmonary artery pressure (mpap), cardiac output (CO), mean arterial pressure (MAP), pulmonary capillary wedge pressure (PCWP) mixed venous oxygen saturation ($SvO_2$%) and systemic arterial oxygen pressure ($PaO_2$%). VIP (100 µg in 3 ml NaCl 0.9%) was inhaled for 15 minutes via the MicroDrop Master Jet (MPV, Truma, Germany) using a particle size of 3 µm to provide alveolar deposition of the substance. Alternatively VIP was injected i.v. 20 (ng/kg.b.w./min) via portable pump system (CADD-1, Pharmacia-Upjohn, Vienna, Austria). Pulmonary homodynamic and gas exchange were measured before and 15 minutes after inhalation or i.v. injection of VIP. Right heart catheterisation was performed in the intensive care unit. The patient was monitored on-line electrocardiographically, invasive blood pressure and systemic arterial oxygen saturation ($SaO_2$%) (Hewlett Packard, Böblingen, Germany) were measured. All hemodynamic and oxygen measurements were performed with a cardiac output computer (Explorer, Baxter) and a pressure monitoring kit (Baxter, Irvine, Calif., USA). Calculations were made according to the standard equations in a patient data management performed by taking blood from the radial and pulmonary artery (Automatic blood gas system, AVL-995-Hb, Austria). Hemodynamic parameters of the PPH patient before and after the acute testing with VIP are summarized in FIGS. 5 and 6, respectively. At baseline (before inhalation of VIP), mPAP was 63 mmHg, CI 3.6 l·min$^{-1}$, PVR 12 woods, PCWP 9 mmHg, $PaO_2$ 91% and $SvO_2$ 61%. Addition of 100 µg inhaled VIP improved pulmonary hemodynamic parameters; mPAP decreased to 49 mmHg and PVR to 9 woods. $PaO_2$ to 93% and $SvO_2$ to 63% compared to baseline.

Example 2

Increased doses of inhaled VIP in a patient suffering from PPH dose-dependently decrease mean pulmonary artery pressure (mPAP) showing maximum efficacy at a dose of 100

Example 3

100 µg of inhaled PACAP time-dependently decrease mean pulmonary artery pressure (mPAP) in a patient with PPH.

Example 4

A patient with severe PPH was under therapy with diltiazem, furosemid and an anticoagulant. Right heart catheterisation (Swan-Ganz, Baxter, Irvine, Calif., USA) was performed to measure mean pulmonary artery pressure (mpap), cardiac output (CO), mean arterial pressure (mAP), pulmonary capillary wedge pressure (PCWP) mixed venous oxygen saturation ($SvO_2$%) and systemic arterial oxygen pressure ($PaO_2$%). PACAP (100 µg in 3 ml NaCl 0.9%) was inhaled for 15 minutes via the MicroDrop Master Jet (MPV, Truma, Germany) using a particle size of 3 µm to provide alveolar deposition of the substance. Pulmonary hemodynamics and gas exchange were measured before and 15 minutes after inhalation of PACAP. Right heart catheterisation was performed in the intensive care unit. The patient was monitored on-line electrocardiographically, invasive blood pressure and systemic arterial oxygen saturation ($SaO_2$%) (Hewlett Packard, Böblingen, Germany) were measured. All hemodynamic and oxygen measurements were performed with a cardiac output computer (Explorer, Baxter) and a pressure monitoring kit (Baxter, Irvine, Calif., USA). Calculations were made according to the standard equations in a patient data management system (CareVue 9000, Hewlett Packard, Böblingen, Germany). Blood gas analysis was performed by taking blood from the radial and pulmonary artery (Automatic blood gas system, AVL-995-Hb, Austria). Hemodynamic parameters of the PPH patient before and after the acute testing with PACAP are summarized in FIG. 5b. At baseline (before inhalation of PACAP), mPAP was 65 mmHg, CI 3.2 l·min$^{-1}$, PVR 13 woods, PCWP 10 mmHg, $PaO_2$ 91% and $SvO_2$ 59%. Addition of 100 µg inhaled PACAP improved pulmonary hemodynamic parameters; mpap decreased to 45 mmHg and PVR to 8 woods. $PaO_2$ increased to 93% and $SvO_2$ to 62% compared to baseline.

TABLE 1

|        | mPAP | CI  | PVR   | PCWP | mAP  | SvO2 | PaO2 |      |
|--------|------|-----|-------|------|------|------|------|------|
| before | 57.1 | 2.7 | 906.4 | 8.6  | 84.5 | 60.0 | 66.8 | mean |
|        | 9.3  | 1.1 | 438.9 | 3.1  | 10.9 | 7.9  | 7.6  | SD   |
| after  | 44.4 | 3.2 | 544.1 | 8.5  | 81.0 | 62.5 | 69.3 | mean |
|        | 11.8 | 1.1 | 213.1 | 2.6  | 6.3  | 7.0  | 11.5 | SD   |

Example 5

A patient suffering from Chronic Obstructive Pulmonary Disease (COPD) with secondary pulmonary hypertension (SPH) (mPAP 32 mmHg) was tested for his response to inhaled VIP (200 µg in 3 ml NaCl 0.9%) The inhalation of VIP led to a decrease of mPAP from 32 mmHg to 25 mmHg. This effect was paralleled by increase of cardiac output from 4.1 l·min$^{-1}$ to 4.8 l·min$^{-1}$.

Example 6

A patient with severe essential arteriolar hypertension is under treatment with nifedipine and enalapril. Systolic and diastolic systemic arterial pressure (SAP) were measured by intraarterial monitoring. VIP (20 ng/kg/min) was injected i.v. via a portable pump system (CADD-1, Pharmacia-Upjohn, Vienna, Austria). The blood pressure lowering effect of VIP is demonstrated in FIG. 7. Before injection of VIP, the systolic pressure (SAP) was 165 mmHg and the diastolic (DAP) was 110 mmHg. The application of VIP resulted in a considerable fall of blood pressure, systolic to 145 mmHg and diastolic to 90 mmHg.

The invention claimed is:

1. A method for treating primary pulmonary hypertension comprising administering to a human patient a polypeptide comprising the following amino acid sequence:
Arg-Lys-Gln-Met-Ala-Val-Lsy-Lys-Tyr-Leu (SEQ ID NO: 4)
by inhalation.

2. The method according to claim 1, wherein said polypeptide further comprises at least one of the following amino acid sequences:
His-Ser-Asp (SEQ ID NO: 14); Phe-Thr-Asp (SEQ ID NO: 13).

3. The method according to claim 1, wherein said polypeptide has the following amino acid sequence:
$(A)_n$-Arg-Lys-Gln-Met-Ala-Val-Lys-Lys-Tyr-Leu-$(B)_m$ ($(A)_n$-SEQ ID NO: 4-$(B)_m$) wherein
$(A)_n$ and $(B)_m$, represent any sequence of naturally occurring amino acid residues, and $(A)_n$ and $(B)_m$ vary independently from each other; and
n and m are integers having values from 0-25, and n and m vary independently from each other.

4. The method according to claim 3, wherein, if n>2, $(A)_n$ has the following sequence:
$(X)_o$-Phe-Thr-Asp-$(Y)_p$($(X)_o$-SEQ ID NO: 13-$(Y)_p$) wherein
$(X)_o$ and $(Y)_p$ represent any sequence of naturally occurring amino acid residues, and
$(X)_o$ and $(Y)_p$ vary independently from each other; and o and p are integers having values from 0-11, and o and p vary independently from each other.

5. The method according to claim 4, wherein, if o>2, $(X)_o$ has the following sequence:
$(X')_q$-His-Ser-Asp-$(X'')_r$($(X')_q$-SEQ ID NO: 14-$(X'')_r$) wherein $(X')_q$ and -$(X'')_r$ represent any sequence of naturally occurring amino acid residues, and $(X')_q$ and -$(X'')_r$ vary independently from each other;
and r and q are integers having values from 0-4, and r and q vary independently from each other.

6. The method according to claim 4, wherein the sequence of said polypeptide is selected from the following group:
(i) Phe-Thr-Asp $X^1$-$X^2$-$X^3$-$X^4$-$X^5$-Arg-Lys-Gln-Met-Ala-Val-Lys-Lys-Tyr-Leu-Asn-Ser-Ile-Leu-Asn (SEQ ID NO: 5);
(ii) Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn (SEQ ID NO: 6);
(iii) Phe-Thr-Asp-Ser-Tyr-Ser-Arg-Tyr-Arg-Lys-Gln-Met-Ala-Val-Lys-Lys-Tyr-Leu (SEQ ID NO: 7)
(iv) His-Ser-Asp-$X^1$-$X^2$-Phe-Thr-Asp-$X^3$-$X^4$-$X^5$-$X^6$-$X^7$-Arg-Lys-Gln-Met-Ala-Val-Lys-Lys-Tyr-Leu (SEQ ID NO: 8);
(v) His-Ser-Asp-Ala-Val-Phe-Thr-Asp-Asn-Tyr-Thr-Arg-Leu-Arg-Lys-Gln-Met-Ala-Val-Lys-Lys-Tyr-Leu (SEQ ID NO: 9);
(vi) His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu (SEQ ID NO: 10);
(vii) His-Ser-Asp-$X^1$-$X^2$-Phe-Thr-Asp-$X^3$-$X^4$-$X^5$-$X^6$-$X^7$-Arg-Lys-Gln-Met-Ala-Val-Lys-Lys-Tyr-Leu-$X^8$-$X^9$-$X^{10}$-$X^{11}$-$X^{12}$ (SEQ ID NO: 11);
(viii) His-Ser-Asp-$X^1$-$X^2$-Phe-Thr-Asp $X^3$-$X^4$-$X^5$-$X^6$-$X^7$-Arg-Lys-Gln-Met-Ala-Val-Lys-Lys-Tyr-Leu-$X^8$-$X^9$-$X^{10}$-$X^{11}$-$X^{12}$-$X^{13}$-$X^{14}$-$X^{15}$-$X^{16}$-$X^{17}$-$X^{18}$-$X^{19}$-$X^{20}$-$X^{21}$-$X^{22}$ (SEQ ID NO: 12);
(ix) His-Ser-Asp-Ala-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn (VIP) (SEQ ID NO: 1);
wherein $X^1$-$X^{22}$ is any naturally occurring amino acid residue.

7. The method according to claim 1, wherein said polypeptide is in a stabilized form.

8. The method according to claim 1, wherein said polypeptide reduces vessel tone of human pulmonary arterial rings.

9. The method according to claim 1, wherein said polypeptide reduces the intracellular free calcium concentration in human vascular smooth muscle cells (VSMC).

10. The method according to claim 1, wherein said polypeptide wherein said polypeptide reduces proliferation of vascular smooth muscle cells (VSMC) of human pulmonary arterial vessels.

11. The method according to claim 1, wherein said disease is right heart failure caused by primary pulmonary hypertension.

12. The method according to claim 1, wherein pulmonary arterial pressure is reduced to more than 20% after administration of said polypeptide.

13. The method of claim 1, wherein diastolic blood pressure associated with primary pulmonary hypertension is reduced to 5-25% and systolic blood pressure associated with primary pulmonary hypertension is reduced to 10-30% after administration of said polypeptide.

14. The method according to claim 7, wherein said polypeptide reduces vessel tone of human pulmonary arterial rings.

15. The method according to claim 7, wherein said polypeptide reduces proliferation of vascular smooth muscle cells (VSMC) of human pulmonary arterial vessels.

16. The method according to claim 7, wherein the disease or a disorder is right heart failure caused by primary pulmonary hypertension.

17. The method according to claim 7, wherein pulmonary arterial pressure is reduced to more than 20% after administration of said polypeptide.

18. The method of claim 7, wherein the disease or a disorder correlated directly or indirectly with hypertension symptoms in human lung and/or heart tissue is arteriolar hypertension associated with primary pulmonary hypertension, wherein diastolic blood pressure associated with primary pulmonary hypertension is reduced to 5-25% and systolic blood pressure is reduced to 10-30% after administration of said polypeptide.

* * * * *